US009801562B1

(12) United States Patent
Host-Madsen

(10) Patent No.: US 9,801,562 B1
(45) Date of Patent: Oct. 31, 2017

(54) CARDIAC MONITORING AND DIAGNOSTIC SYSTEMS, METHODS, AND DEVICES

(71) Applicant: University of Hawaii, Honolulu, HI (US)

(72) Inventor: Anders Host-Madsen, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 415 days.

(21) Appl. No.: 14/727,706

(22) Filed: Jun. 1, 2015

Related U.S. Application Data

(60) Provisional application No. 62/168,555, filed on May 29, 2015, provisional application No. 62/006,612, filed on Jun. 2, 2014.

(51) Int. Cl.
*A61B 5/0402* (2006.01)
*A61B 5/04* (2006.01)
*A61B 5/0452* (2006.01)
*A61B 5/00* (2006.01)

(52) U.S. Cl.
CPC ........ *A61B 5/04018* (2013.01); *A61B 5/0452* (2013.01); *A61B 5/7246* (2013.01); *A61B 5/7267* (2013.01); *A61B 5/7275* (2013.01)

(58) Field of Classification Search
CPC . A61B 5/04018; A61B 5/0452; A61B 5/7246; A61B 5/7267; A61B 5/7275
USPC .......................................................... 600/515
See application file for complete search history.

(56) References Cited

U.S. PATENT DOCUMENTS

| | | | |
|---|---|---|---|
| 6,370,423 B1* | 4/2002 | Guerrero | A61B 5/044 600/509 |
| 7,930,256 B2 | 4/2011 | Gonsalves et al. | |
| 8,150,783 B2 | 4/2012 | Gonsalves et al. | |
| 8,407,791 B2 | 3/2013 | Granstedt et al. | |
| 8,595,831 B2 | 11/2013 | Skare | |
| 8,726,393 B2 | 5/2014 | Macy et al. | |
| 8,856,936 B2 | 10/2014 | Datta Ray et al. | |
| 8,881,288 B1 | 11/2014 | Levy et al. | |
| 8,914,880 B2 | 12/2014 | Lee | |
| 8,925,083 B2 | 12/2014 | Niner et al. | |
| 8,977,843 B2 | 3/2015 | Gutt et al. | |
| 9,032,521 B2 | 5/2015 | Amini et al. | |
| 2008/0243209 A1* | 10/2008 | Corndorf | A61B 5/0006 607/60 |
| 2012/0123232 A1* | 5/2012 | Najarian | A61B 5/0022 600/345 |

(Continued)

*Primary Examiner* — Carl H Layno
*Assistant Examiner* — Erin M Piateski
(74) *Attorney, Agent, or Firm* — Knobbe Martens Olson & Bear LLP

(57) ABSTRACT

The disclosure herein provides cardiac monitoring and diagnostic system, methods, and devices. A cardiac diagnostic system for detecting potential indicators of cardiac disease comprises: a cardiac monitoring device comprising at least one electrode configured to detect an analog electrical cardiac signal of a user; a cardiac signal filter configured to convert the analog electrical cardiac signal to digital electrocardiogram data; an atypical cardiac sequence detector configured to detect atypical cardiac patterns in the electrocardiogram data that are potentially indicative of cardiac disease; and a notification transmitter configured to generate an alert when a detected atypical cardiac pattern is determined to be indicative of cardiac disease.

20 Claims, 12 Drawing Sheets

(56) References Cited

U.S. PATENT DOCUMENTS

2014/0213919 A1* 7/2014 Poon ................. A61B 5/02405
600/509
2014/0330159 A1* 11/2014 Costa ................. A61B 5/1124
600/558

* cited by examiner

CARDIAC MONITORING AND DIAGNOSTIC SYSTEMS, METHODS, AND DEVICES

CROSS-REFERENCE TO RELATED APPLICATIONS

This application claims the benefit of U.S. Provisional Application No. 62/168,555, filed May 29, 2015, and U.S. Provisional Application No. 62/006,612, filed Jun. 2, 2014. Each of the foregoing applications is hereby incorporated by reference herein in its entirety.

STATEMENT REGARDING FEDERALLY SPONSORED R&D

This invention was made with government support under CCF 1017823, 1017775, and 1434600 awarded by the National Science Foundation. The government has certain rights in the invention.

BACKGROUND

Field

The disclosure relates generally to the field of medical devices, and more specifically to cardiac monitoring and diagnostic systems, methods, and devices.

Description

Cardiac disease is one of the biggest killers of adults in the U.S. and elsewhere. Early detection of cardiac disease can greatly increase the chances of survival and/or extension of life. Various medical devices have been developed that help a physician to diagnose cardiac disease and potentially detect signs of cardiac disease. For example, a physician may have a patient undergo an electrocardiogram (ECG or EKG) test that monitors electrical activity related to the patient's heart. The ECG results may then be analyzed to determine whether there are any known indicators of heart disease. While such techniques can be useful, there is a need for systems and techniques for earlier and more accurate detection of cardiac disease.

SUMMARY

The disclosure herein provides cardiac monitoring and diagnostic systems, methods, and devices. The cardiac monitoring systems disclosed herein may be utilized to, for example, detect potential signs of cardiac disease in a patient. In some embodiments, the systems and methods disclosed herein are configured to detect signs of cardiac disease and/or atypical cardiac function that were previously unknown as being signs of potential cardiac disease. Accordingly, the techniques disclosed herein enable more efficient and earlier diagnosis of potential cardiac disease.

According to some embodiments, a cardiac diagnostic system for detecting potential indicators of cardiac disease comprises: a cardiac monitoring device comprising at least one electrode configured to detect an analog electrical cardiac signal of a user; a cardiac signal filter configured to convert the analog electrical cardiac signal to digital electrocardiogram data; an atypical cardiac sequence detector configured to detect atypical cardiac patterns in the electrocardiogram data that are potentially indicative of cardiac disease; and a notification transmitter configured to generate an alert when a detected atypical cardiac pattern is determined to be indicative of cardiac disease.

According to some embodiments, a cardiac diagnostic system for detecting potential indicators of cardiac disease comprises: a cardiac monitoring device comprising at least one electrode configured to detect an analog electrical cardiac signal of a user; a cardiac signal filter configured to convert the analog electrical cardiac signal to digital electrocardiogram data; and an atypical cardiac sequence detector configured to analyze the digital electrocardiogram data to detect atypical cardiac patterns that are potentially indicative of cardiac disease, wherein detecting the atypical cardiac patterns comprises: determining a first encoded length of a segment of the digital electrocardiogram data using an encoder based on typical data; determining a second encoded length of the segment of the digital electrocardiogram data using a second encoder without knowledge of typical data, making sure that the encoded data is decodable; and comparing the first and second encoded lengths, wherein the second encoded length being smaller than the first encoded length is indicative of an atypical cardiac pattern.

According to some embodiments, a cardiac diagnostic system for detecting potential indicators of cardiac disease comprises: a cardiac monitoring device comprising at least one electrode configured to detect an analog electrical cardiac signal of a user; a cardiac signal filter configured to convert the analog electrical cardiac signal to digital electrocardiogram data; and an atypical cardiac sequence detector configured to analyze the digital electrocardiogram data to detect atypical cardiac patterns that are potentially indicative of cardiac disease, wherein detecting the atypical cardiac patterns comprises: determining a first encoded length of a segment of the digital electrocardiogram data using a first encoder (in some embodiments, an encoder based on typical data); determining a second encoded length of the segment of the digital electrocardiogram data using a second encoder (in some embodiments, without knowledge of typical data, and in some embodiments making sure that the encoded data is decodable); and comparing the first and second encoded lengths, wherein the second encoded length being smaller than the first encoded length is indicative of an atypical cardiac pattern.

In some embodiments, the cardiac diagnostic system further comprises: an atypical cardiac sequence processor configured to analyze detected atypical cardiac patterns in conjunction with historical data to determine whether the detected cardiac patterns are indicative of cardiac disease. In some embodiments, the atypical cardiac sequence processor is further configured to generate an alert when a detected atypical cardiac pattern is determined to be indicative of cardiac disease. In some embodiments, the first encoder comprises a typical encoder and the second encoder comprises a universal encoder. In some embodiments, the first encoder comprises a universal encoder that has been trained and frozen. In some embodiments, the second encoder comprises the same universal encoder, but not having been frozen. In some embodiments, the atypical sequence detector is further configured to store a detected pattern in a known patterns database. In some embodiments, detecting the atypical cardiac patterns further comprises: determining a difference in the first and second encoded lengths; comparing the determined difference to a threshold value; and flagging the segment as atypical when the determined difference is greater than the threshold value. In some embodiments, the cardiac diagnostic system further comprises one or more computer processors configured to operate the cardiac signal filter and atypical cardiac sequence detector.

According to some embodiments, a cardiac diagnostic system for detecting potential indicators of cardiac disease comprises: an atypical cardiac sequence detector configured to analyze digital electrocardiogram data to detect atypical cardiac patterns that are potentially indicative of cardiac disease, the digital electrocardiogram data generated by a cardiac signal filter configured to convert analog electrical cardiac signals to digital data, the analog electrical cardiac signals detected by at least one electrode of a cardiac monitoring device, wherein detecting the atypical cardiac patterns comprises: determining a first encoded length of a segment of the digital electrocardiogram data using an encoder based on typical data; determining a second encoded length of the segment of the digital electrocardiogram data using an encoder without knowledge of typical data, making sure that the encoded data is decodable; and comparing the first and second encoded lengths, wherein the second encoded length being smaller than the first encoded length is indicative of an atypical cardiac pattern.

According to some embodiments, a cardiac diagnostic system for detecting potential indicators of cardiac disease comprises: an atypical cardiac sequence detector configured to analyze digital electrocardiogram data to detect atypical cardiac patterns that are potentially indicative of cardiac disease, the digital electrocardiogram data generated by a cardiac signal filter configured to convert analog electrical cardiac signals to digital data, the analog electrical cardiac signals detected by at least one electrode of a cardiac monitoring device, wherein detecting the atypical cardiac patterns comprises: determining a first encoded length of a segment of the digital electrocardiogram data using a first encoder (in some embodiments, an encoder based on typical data); determining a second encoded length of the segment of the digital electrocardiogram data using a second encoder (in some embodiments, an encoder without knowledge of typical data, in some embodiments making sure that the encoded data is decodable); and comparing the first and second encoded lengths, wherein the second encoded length being smaller than the first encoded length is indicative of an atypical cardiac pattern.

In some embodiments, the cardiac diagnostic system further comprises: an atypical cardiac sequence processor configured to analyze detected atypical cardiac patterns in conjunction with historical data to determine whether the detected cardiac patterns are indicative of cardiac disease. In some embodiments, the atypical cardiac sequence processor is further configured to generate an alert when a detected atypical cardiac pattern is determined to be indicative of cardiac disease. In some embodiments, the first encoder comprises a typical encoder and the second encoder comprises a universal encoder. In some embodiments, the first encoder comprises a universal encoder that has been trained and frozen. In some embodiments, the second encoder comprises the same universal encoder, but not having been frozen. In some embodiments, the atypical sequence detector is further configured to store a detected pattern in a known patterns database. In some embodiments, detecting the atypical cardiac patterns further comprises: determining a difference in the first and second encoded lengths; comparing the determined difference to a threshold value; and flagging the segment as atypical when the determined difference is greater than the threshold value. In some embodiments, the cardiac diagnostic system further comprises one or more computer processors configured to operate the atypical cardiac sequence detector.

According to some embodiments, a cardiac diagnostic method for detecting potential indicators of cardiac disease comprises: receiving, by a computer system, digital electrocardiogram data representative of electrical cardiac activity, the digital electrocardiogram data generated by converting analog electrical cardiac signals to digital data, the analog electrical cardiac signals detected by at least one electrode of a cardiac monitoring device; selecting, by the computer system, a segment of the digital electrocardiogram data to analyze for potential atypical cardiac patterns; determining, by the computer system, a first encoded length of the segment of the digital electrocardiogram data using an encoder based on typical data; determining, by the computer system, a second encoded length of the segment of the digital electrocardiogram data using an encoder without knowledge of typical data, making sure that the encoded data is decodable; and comparing, by the computer system, the first and second encoded lengths, wherein the second encoded length being smaller than the first encoded length is indicative of an atypical cardiac pattern, and wherein the computer system comprises one or more computer processors and an electronic memory. In some embodiments, the first encoder comprises a typical encoder and the second encoder comprises a universal encoder.

According to some embodiments, a cardiac diagnostic method for detecting potential indicators of cardiac disease comprises: receiving, by a computer system, digital electrocardiogram data representative of electrical cardiac activity, the digital electrocardiogram data generated by converting analog electrical cardiac signals to digital data, the analog electrical cardiac signals detected by at least one electrode of a cardiac monitoring device; selecting, by the computer system, a segment of the digital electrocardiogram data to analyze for potential atypical cardiac patterns; determining, by the computer system, a first encoded length of the segment of the digital electrocardiogram data using a first encoder (in some embodiments, using an encoder based on typical data); determining, by the computer system, a second encoded length of the segment of the digital electrocardiogram data using a second encoder (in some embodiments, using an encoder without knowledge of typical data, in some embodiments making sure that the encoded data is decodable); and comparing, by the computer system, the first and second encoded lengths, wherein the second encoded length being smaller than the first encoded length is indicative of an atypical cardiac pattern, and wherein the computer system comprises one or more computer processors and an electronic memory. In some embodiments, the first encoder comprises a typical encoder and the second encoder comprises a universal encoder.

In some embodiments, a method for detecting atypical data comprises: receiving, by a computer system, data for analysis; selecting, by the computer system, a segment of the received data to analyze for atypical patterns; determining, by the computer system, a first encoded length of the segment of the received data using a first encoder based on typical data; determining, by the computer system, a second encoded length of the segment of the received data using a second encoder without knowledge of typical data, so that the encoded data is decodable; and comparing, by the computer system, the first and second encoded lengths, wherein the second encoded length being smaller than the first encoded length is indicative of an atypical pattern, and wherein the computer system comprises one or more computer processors and an electronic memory. In some embodiments, a method for detecting atypical data comprises: receiving, by a computer system, data for analysis; selecting, by the computer system, a segment of the received data to analyze for atypical patterns; determining, by the computer system, a first encoded length of the segment of the received data using a first encoder (in some embodiments, an encoder based on typical data); determining, by the computer system, a second encoded length of the segment of the received data using a second encoder (in some embodiments, an encoder without knowledge of typical data, in some embodiments so that the encoded data is decodable); and comparing, by the computer system, the first and second encoded lengths, wherein the second encoded length being smaller than the first encoded length is indicative of an atypical pattern, and wherein the computer system comprises one or more computer processors and an electronic memory.

In some embodiments, a computer-implemented method for assisting a user in detecting atypical data stored or represented in a computer data repository is disclosed. In an embodiment, the computer-implemented method comprises selecting, by the computer system, a data set for analysis to determine atypical data within the data set. The computer-implemented method can also comprise generating, by the computer system, a first encoded length of a segment of the data set using an encoder based on typical data (and/or in some embodiments a first encoder). The computer-implemented method can also comprise generating, by the computer system, a second encoded length of the segment of the data set using an encoder without knowledge of typical data, making sure that the encoded data is decodable (and/or using a second encoder, and, in some embodiments not necessarily making sure that the encoded data is decodable). The computer-implemented method can also comprise comparing, by the computer system, the first and second encoded lengths. The computer-implemented method can also comprise determining whether the second encoded length is smaller than the first encoded length, wherein the second encoded length being smaller than the first encoded length is indicative of an atypical pattern. The computer-implemented method can also comprise generating interface data configured to dynamically render a user interface that provides functionality for the user to interact with a graphical representation of the atypical pattern in the context of a portion of the data set, wherein interaction with the graphical representation comprises at least one of selecting an action in response to the atypical pattern, and selecting an alternate view of the atypical pattern. The computer-implemented method can be implemented using a computer system comprising one or more computer processors and an electronic memory. The computer-implemented method can also comprise wherein the data set is a data stream generated in real time from a data generator. In an embodiment, the computer-implemented method can be utilized in a cardiac diagnostic system. In an embodiment, the computer-implemented method can utilized in the cybersecurity context, for example, to detect cyber-attacks of computer networks, or utilized for detecting insider trading, credit card fraud, illicit art deals, piracy, monitoring of vast amounts of electronic (digital or analog) indications, video surveillance, monitoring of computer network searches in Internet search engines, auditing financial data, terrorism, and/or the like. Further, the computer-implemented method may have a plurality of uses in analyzing large datasets to determine atypical or interesting data in such datasets. For example, the computer-implemented method may be useful in analyzing stocks, vast amounts of textual materials, medical information for medical trials, image databases, medical research, climate research, environmental research, seismic research, genomics, scientific data, business data, and/or social networks. The computer-implemented method may also have applications in, for example, devices such as airplanes and cars or utility networks.

BRIEF DESCRIPTION OF THE DRAWINGS

The foregoing and other features, aspects, and advantages of the present invention are described in detail below with reference to the drawings of various embodiments, which are intended to illustrate and not to limit the invention. The drawings comprise the following FIGS. in which.

DETAILED DESCRIPTION OF THE EMBODIMENTS

Figure 1A:
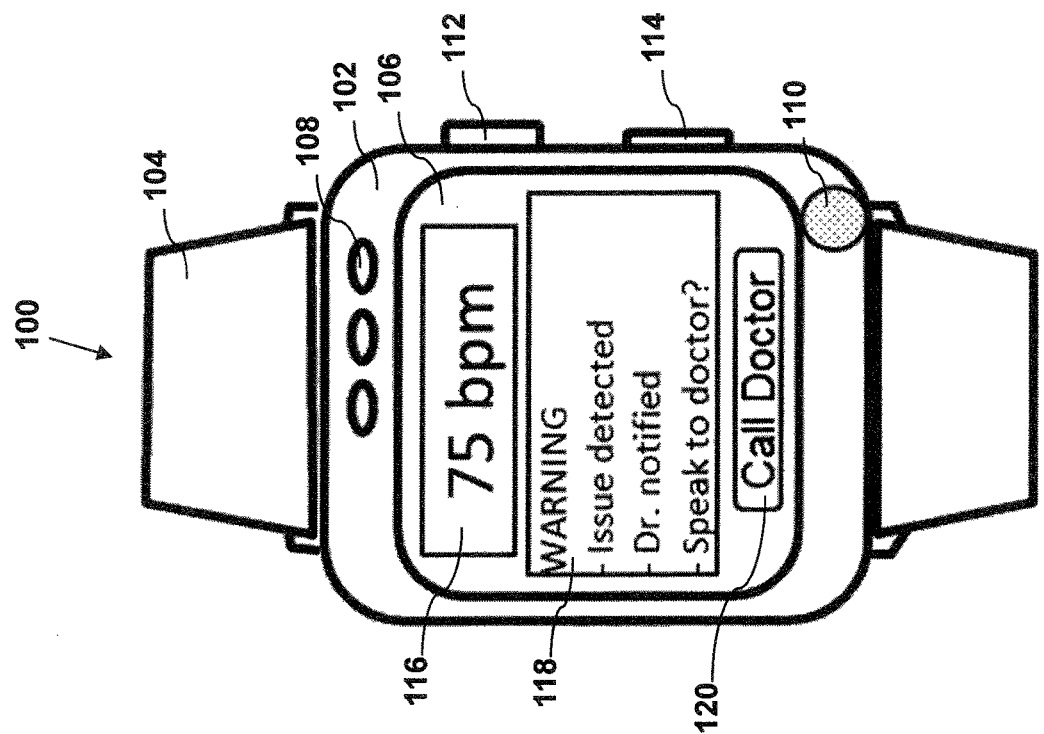
FIG. 1A is a front view of an embodiment of a cardiac monitoring device.

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying FIGS., wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described. Further, it should be understood that any of the examples herein are non-limiting. As such, the inventions disclosed herein are not limited to any particular embodiments, aspects, concepts, structures, functionalities, or examples described herein.

Cardiac disease, or heart disease, is a major issue in today's society. Cardiac disease, often resulting in a heart attack and/or complete cardiac failure, is one of the top killers of adults in the U.S. and worldwide. Accordingly, various techniques and systems have been developed to detect and treat cardiac disease. For example, one technique used to detect and/or diagnose cardiac disease is an electrocardiogram or ECG. An ECG test detects and logs electrical signals in a human that are related to heart function. By logging such signals, a doctor can analyze a chart of the logged signals to determine if there are any known patterns of irregularities or other cardiac disease indicators. For example, a doctor may be able to review an ECG log to determine whether heartbeats are irregularly spaced, and/or to determine various other potential cardiac issues. This is one important method of diagnosing cardiac disease; namely, comparing a patient's ECG to known patterns that are indicative of cardiac disease.

The cardiac monitoring systems, methods, and devices disclosed herein present a significant step forward in early and accurate detection of cardiac disease in humans. As mentioned above, a typical method of diagnosing or detecting cardiac disease is comparing a patient's heartbeat or ECG signals to known patterns that indicate cardiac disease. However, each patient is different, and each patient's cardiac disease may present itself in a different manner. Further, there are a large number of, likely an infinite number of, additional patterns in ECG signals that are indicative of cardiac issues, but that no current systems or techniques are aware of and/or are capable of detecting, because those patterns are not yet known. The systems disclosed herein are a significant development in the fight against cardiac disease, because the systems are able to detect any abnormality or atypicality in a patient's cardiac operation, even if that abnormality or type of abnormality has never been noticed before, has never been detected before, has never been noticed to be an abnormality, and/or has never been realized as being a cardiac disease indicator.

In some embodiments, as further described in greater detail below, a cardiac monitoring and diagnostic system is disclosed that comprises a cardiac monitoring device configured to be worn by a patient for an extended period of time. The cardiac monitoring device is configured to desirably continually or intermittently monitor the patient's electrocardiogram signals and detect any atypical or abnormal patterns in the patient's cardiac function, even if such irregularities or abnormalities have never been known before and/or never been known before to be an indicator for cardiac disease. In some embodiments, the system is configured to detect and report any anomalies or abnormalities, without determining whether such abnormality or anomaly is indicative of cardiac disease. However, in other embodiments, the cardiac monitoring system comprises further functionality that analyzes the detected abnormalities to determine whether those abnormalities are potentially indicative of cardiac disease.

Figure 1B:
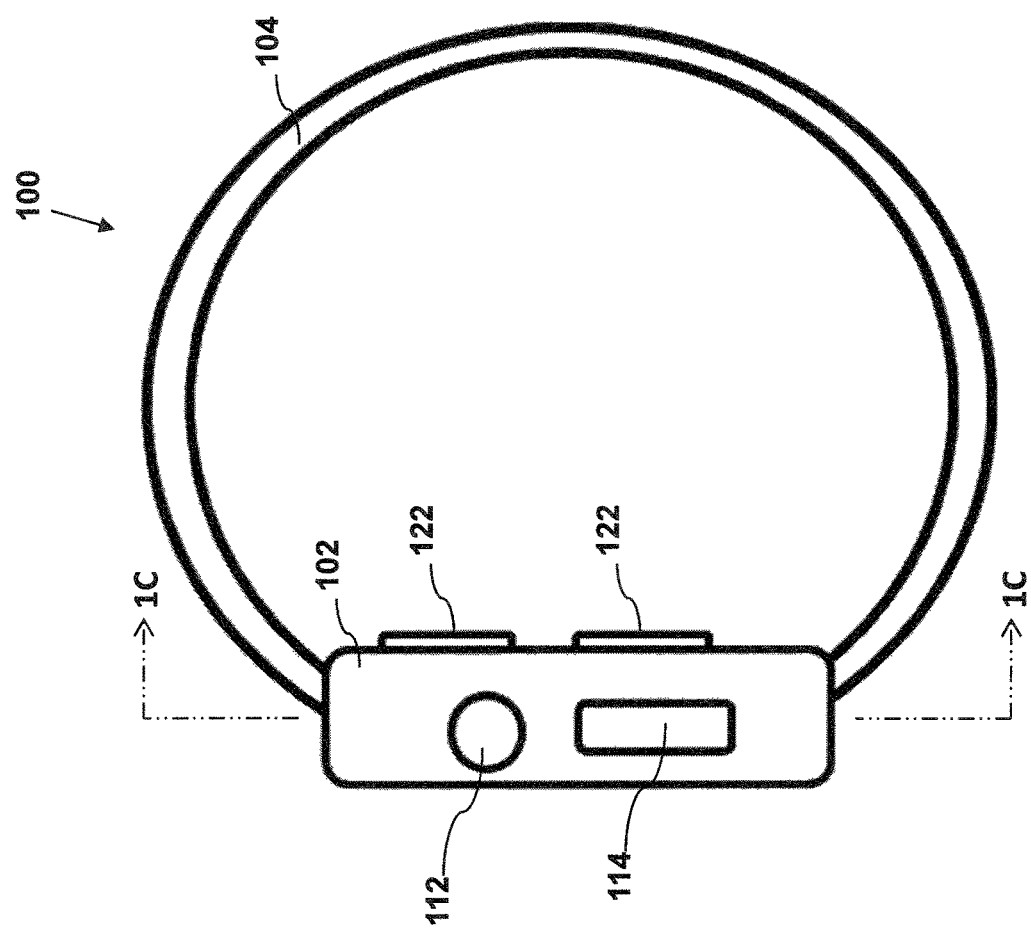
FIG. 1B is a side view of the cardiac monitoring device of FIG. 1A.
Figure 1C:
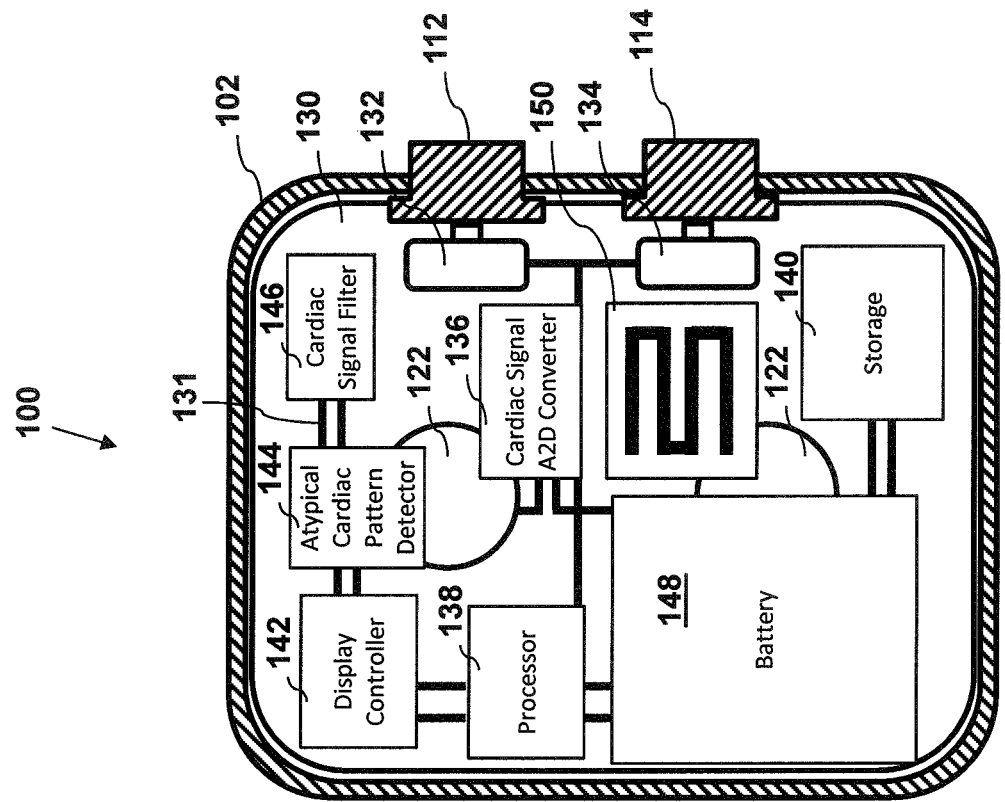
FIG. 1C is a cross-sectional view of the cardiac monitoring device of FIG. 1A.

As will be further described below, one embodiment of such a cardiac monitoring device is illustrated in FIGS. 1A through 1C. The cardiac monitoring device 100 in this embodiment comprises a device configured to be worn by a user (e.g., a smart watch or similar device), the device comprising and/or being operably connected either by wires or wirelessly to electrodes 122 configured to contact the user's skin and receive electrical signals indicative of cardiac activity. Such a cardiac monitoring device is convenient because it can simply be worn as a watch and is not otherwise intrusive, and lets the patient go about their typical day. In some embodiments, the cardiac monitoring device or smart watch type device includes further functionality to automatically or dynamically enable a notification or alert to be sent to the patient and/or to the patient's doctor indicating when an abnormality has been detected. In some embodiments, the cardiac monitoring device may further comprise the ability to open up a direct line of communication between the patient and his or her doctor. For example, when an abnormality has been detected, a button may appear on the graphical user interface of the smart watch that enables the patient to directly contact his or her doctor by, for example, placing a telephone call to the doctor using a Bluetooth enabled smart phone connected to the cardiac monitoring device. Although the embodiment illustrated in FIGS. 1A-1C is a watch-type device, various other embodiments may utilize other form factors, such as a device strapped to or otherwise connected to a patient's chest, wrapped around a patient's neck like a necklace, a device carried in the patient's pocket, a head-mounted device (for example, included in a headband or baseball cap), and/or the like, or even a device with one or more components implanted under a patient's skin.

In some embodiments, a cardiac monitoring device as disclosed herein is configured to be worn by a user over an extended period of time and to log cardiac activity data, e.g. ECG data, over that extended period of time. In some embodiments, the cardiac monitoring device may also have the functionality discussed above regarding real time monitoring and notifications. However, such a device may also comprise functionality to log the cardiac activity data, in its raw form and/or in a processed or encoded form, and to upload that logged data to a physician's cardiac analysis system, and/or to a third-party cardiac analysis system. For example, one use of such a device may be to enable a physician to review a patient's cardiac data from the last second, minute, hour, day, week, month, six or 12 months, years, or for example any other time period between doctor's office visits. In some embodiments, the cardiac monitoring device itself, and/or a physician's system or third-parry's system is configured to further analyze the logged data as further described below, to detect and/or process atypical or anomalous segments in the data that may potentially be indicators of cardiac disease. In some embodiments, the device can also contain a button or other functionality to allow a patient to notify the device that they are having symptoms such as chest pain, dizziness, shortness of breath, or palpitations for example, and the device can be configured to correlate the symptoms to the logged data akin to an event monitor. As mentioned above, the system can be configured to not only detect anomalies that are previously known as indicators of cardiac disease, but also anomalies that were not previously known to be indicators of cardiac disease and/or not even previously known as being an anomaly. For example, the systems and techniques disclosed herein are capable of detecting anomalies and data that a human or a past system would not have even identified as an anomaly. Accordingly, the systems, methods, and devices disclosed herein enable faster, earlier, and more efficient detection of cardiac disease, potentially enabling the saving of countless lives, decreasing morbidity and/or hospitalizations.

As will be discussed in greater technical detail below, one advantage of the cardiac monitoring systems disclosed herein is that they are capable of detecting previously unknown patterns. Past cardiac diagnostic systems have been focused on detecting known patterns of cardiac disease indicators. While such systems work relatively well at the task they are designed to do, such systems are hamstrung by the fact that they are only able to detect cardiac disease indicators that have previously been manually determined by a cardiac specialist as something indicative of cardiac disease. Accordingly, there are millions of people walking around that may have detectable, subclinical cardiac disease indicators that are not currently detectable because no one has figured out yet that those indicators or anomalies are indicative of cardiac disease, and/or that those indicators or anomalies even exist. Further, for each patient that is even in the earliest stages of cardiac disease, their cardiac system may show different signs than any other patient. Current systems on the market have no way of interpreting or even detecting these personalized abnormalities or anomalies. Such personalized abnormalities or anomalies may present themselves as a specific pattern or sequence in ECG data that is not apparent to a human observer or to any existing computer system. The systems disclosed herein, however, are designed to detect these early warning signs of cardiac disease, even if the early warning signs present themselves as a specific unique abnormality or anomaly in a specific person's cardiac function that would not be detectable by any other cardiac system on the market. Accordingly, the cardiac monitoring systems disclosed herein can be highly beneficial in saving lives and extending lives by early detection of cardiac disease. Additionally, the systems, methods, and devices disclosed herein for detecting atypical data and/or patterns in data, events, activity, data streams, or the like, can also be applied not only to cardiac diagnostic systems but also to other data sets in order to detect or help identify possible atypical data and/or patterns in the context cybersecurity, financial analysis, scientific research, or the like.

Wearable Cardiac Monitoring and Diagnostic Device

FIGS. 1A-1C illustrate one embodiment of a cardiac monitoring and diagnostic device 100 configured to be worn on a user's wrist, as disclosed herein. In some embodiments, the cardiac monitoring device 100 is a purpose-built device that performs only cardiac monitoring and/or related functions. However, in other embodiments, the cardiac monitoring device 100 may comprise other features unrelated to cardiac monitoring. For example, the cardiac monitoring device 100 may comprise a smart watch, such as a device that enables the user to perform various other functions, such as tell the time, get directions using a built-in GPS unit and a maps application, make calculations with a calculator application, and/or perform various other functions unrelated to cardiac monitoring. The majority of the description related to FIGS. 1A through 1C will, however, be focused on the cardiac monitoring and diagnostic functions of the cardiac monitoring device 100.

FIG. 1A is a front view of the cardiac monitoring device 100. FIG. 1B is a side view of the cardiac monitoring device 100. FIG. 1C is a cross sectional view of the cardiac monitoring device, as sectioned as shown in FIG. 1B. Cardiac monitoring device 100 comprises a main housing 102 coupled to a band or wrist strap 104. The band or wrist strap 104 is desirably flexibly or pivotally coupled to the housing 102 to enable a user to comfortably fit the device to his or her wrist. In this embodiment, the band or wrist strap 104 is shown as a continuous band. However, in various other embodiments, the band 104 may comprise a clasp or similar feature to open the band and/or expand or contract the band to enable removal and fitting of the cardiac monitoring device 100 to the user's wrist. In some embodiments, the band 104 is stretchable or elastic to enable a more comfortable fit.

The cardiac monitoring device 100 in this embodiment comprises two electrodes 122 as illustrated in FIG. 1B. The electrodes 122 are positioned on a back surface of the housing 102. The electrodes 122 are positioned on the back face of the housing 102 so that they can be in constant or relatively regular contact with a user's skin. The electrodes 122 can be configured to create an electrical connection with the user's skin to enable the cardiac monitoring device 100 to detect ECG or electrocardiogram signals that are indicative of cardiac activity of the user. In some embodiments, the electrodes 122 may be attached over or proximate the chest area and are operably connected via wires or wirelessly to the device 100. In some embodiments, the device 100 can be connected or connectable to 2, 3, 4, 5, 6, 7, 8, 9, 10, 11, 12, or more electrodes, or ranges including any of the aforementioned values.

The cardiac monitoring device 100 further comprises various input/output features and multimedia features. For example, the cardiac monitoring device 100 comprises an electronic display 106. In this embodiment the electronic display 106 is touch-sensitive, meaning a user can interact with the device by touching the display, dragging things around the display, and/or the like. Additional input devices or features of the cardiac monitoring device 100 are two buttons 112, 114 and a combined speaker/microphone unit 110. Output devices comprise the speaker/microphone unit 110 and a plurality of LEDs 108. Further, as will be described in greater detail below, the cardiac monitoring device 100 comprises a wireless antenna 150 that enables the cardiac monitoring device 100 to communicate with other devices or systems, such as the user's personal computer, a third-party system, a medical facility or physician's system, a smartphone, and/or the like. In some embodiments, the cardiac monitoring device may comprise additional or fewer input and/or output features. For example, the cardiac monitoring device may comprise a physical computer connector, such as a micro USB port and/or the like.

With further reference to FIG. 1A, in the present example, the electronic display 106 is indicating a variety of pieces of information. Toward a top of the display 106, is a heart rate display 116. In this embodiment, the cardiac monitoring device 100 is indicating to the user that their current heart rate is 75 bpm. The heart rate display 116 may be configured to automatically update at certain intervals. For example, the heart rate display 116 may be configured to update substantially in real time and/or at intervals of less than one second, one second, five seconds, 10 seconds, 20 seconds, 30 seconds, or longer or shorter. Such a feature may be desirable, for example, to enable a user to use the cardiac monitoring device 100 as not only an issue detection device, but also as a fitness device that enables the user to monitor his or her own heart rate, for example, while he or she is exercising. Various studies have shown that a user can get the maximum value out of an exercise routine by maintaining his or her heart rate within a target range. Accordingly, a cardiac monitoring device 100 such as is disclosed herein may be utilized as a device that enables a user to more easily retain his or her heart rate within that target range.

In some embodiments, the cardiac monitoring device 100 can be configured to monitor a user's heart rate and notify the user and/or a third-party when the user's heart rate goes out of a desired threshold range, either above or below the range. However, the cardiac monitoring device 100 can be more sophisticated than simply monitoring a user's heart rate. As will be described in greater detail below, the cardiac monitoring device 100 is desirably configured to monitor a user's cardiac activity and detect any anomalies or abnormalities or atypical segments or sequences in the monitored cardiac activity, whether or not the abnormality has anything to do with a particular heart rate, and to then take some action based on that detected abnormality. In some embodiments, the action is simply to flag that abnormality for later processing or analysis. However, in other embodiments, the desired action is to issue some sort of notification or warning, if, for example, the abnormality is determined to potentially be an indicator of cardiac disease.

The embodiment illustrated in FIG. 1A is illustrating just such an example where the cardiac monitoring device 100 has detected one or more atypicalities or abnormalities that could potentially be an indicator of cardiac disease. Note that in this case, the user's heart rate as indicated by the heart rate display 116 as being 75 bpm. This is a relatively typical resting heart rate for a human. However, cardiac disease can present itself at any time, not just when a heart rate is out of some predetermined threshold range. Accordingly, even in this case, where a user has a typical average resting heart rate, the cardiac monitoring device 100 was able to detect an abnormality or potential indicator of cardiac disease.

With further reference to FIG. 1A, a notification section 118 of the electronic display 106 is indicating to the user that an issue has been detected. In this case, the notification section 118 says WARNING in all capital letters and tells the user that an issue has been detected and that the user's doctor has been notified of this issue. In some embodiments, the device 100 can be configured for a plurality of different (e.g., escalating) notifications depending on the degree of abnormality measured by the device 100. Further, the notification section 118 is asking the user if the user would like to speak to, text, or otherwise communicate with his or her doctor. If the user would like to immediately speak to his or her doctor, the user can conveniently press the call doctor button 120, which in this case is a virtual button presented on the touch sensitive display 106, but in other embodiments may be a physical button, to enable the user to be directly connected to his or her doctor, emergency medical services (e.g., 911), a caregiver, and the like. As mentioned above, this connection may be made directly from the cardiac monitoring device 100 to a device of the doctor, or may be passed through one or more external devices, such as through a Bluetooth enabled cell phone or smart phone connected to the cardiac monitoring device 100 using a wireless radio. In some embodiments, the device 100 may also or alternatively issue an audible and/or visual alert using speaker 110 and/or LED's 108, a haptic vibration, or other alert.

As will be discussed in greater detail below, in some embodiments, the cardiac monitoring device 100 comprises all the functionality needed to both monitor cardiac activity and analyze or process that cardiac activity to detect abnormalities or atypicalities that may be indicative of cardiac disease. In some embodiments, however, the cardiac monitoring device 100 is configured to collect the raw ECG data and forwarded it on (either as raw data or at least partially processed, filtered, converted, and/or compressed) to an external system for processing and/or detection of abnormalities.

FIG. 1C illustrates a cross-sectional view of the main housing 102 of the cardiac monitoring device 100. This cross-sectional view illustrates various components of this embodiment of a cardiac monitoring device that enables this embodiment of a cardiac monitoring device to monitor cardiac activity and detect abnormalities in that cardiac activity. As shown in FIG. 1C, the housing 102 has a circuit board or PCB 130 disposed therein. That PCB 130 comprises a plurality of electrical traces 131 connecting a plurality of functional components. Among these functional components are switches 132, 134 configured to enable detection of button presses of the buttons 112, 114. The cardiac monitoring device 100 further comprises a cardiac signal analog-to-digital converter 136 that is in electronic communication with the two electrodes 122. The cardiac signal A2D converter 136 is configured to convert analog electrical signals coming from the electrodes 122 into digital data that can then be stored in storage 140, which in some embodiments may comprise flash memory, a hard drive, RAM, and/or any other type of suitable electronic computer memory.

The cardiac monitoring device 100 further comprises a processor 138 (for example, a microcontroller or other computer processor) configured to control various functions of the cardiac monitoring device 100. In some embodiments, the processor 138 controls all or substantially all electronic functions of the cardiac monitoring device 100. In other embodiments, however, at least some other components, such as a function-specific integrated circuit (IC), may be configured to perform specific functions or control specific functions, such as to offload a processor intensive function from the main processor 138. For example, in this embodiment, the cardiac monitoring device 100 further comprises a display controller 142 configured to control the display 106 seen in FIG. 1A. In some embodiments, the display controller 142 handles both the display output and any touch inputs. However, in other embodiments, the touch inputs are handled by another portion of the device, such as the processor 138 or another I/O component.

The cardiac monitoring device 100 in this embodiment further comprises a cardiac signal filter 146 configured to perform filtering of the cardiac activity data. An atypical cardiac pattern detector 144 is configured to analyze the cardiac activity data, either filtered or unfiltered, and to detect atypical or abnormal patterns in that data. Various techniques of performing this detection are described below in greater detail. As mentioned above, the cardiac monitoring device 100 further comprises an internal antenna 150 configured to enable the cardiac monitoring device 100 to wirelessly communicate with one or more external devices, such as, for example, a smart phone, a wireless Wi-Fi network, a cellular network, and/or the like.

Cardiac monitoring device 100 further comprises a battery 148 or other power source configured to power its various functions. The battery 148 may be, for example, a lithium-ion battery and/or various other suitable battery technologies, disposable or rechargeable. In some embodiments, the battery 148 is configured to be user replaceable. In other embodiments, the battery 148 is not intended to be user replaceable, such as to enable the cardiac monitoring device 100 to be of a slimmer profile, of a simpler design, and/or more aesthetically pleasing.

Cardiac Monitoring System

Figure 2:
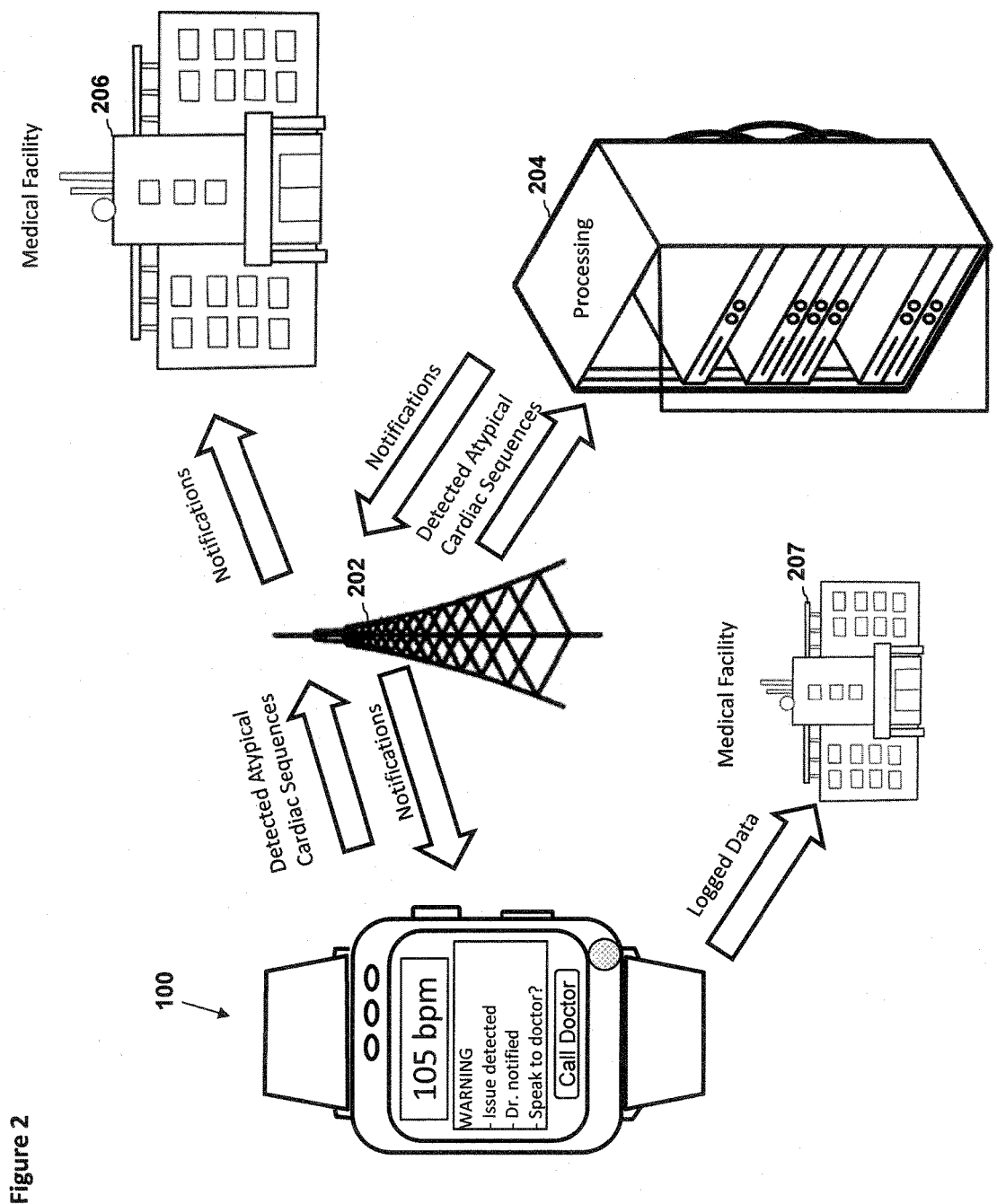
FIG. 2 is a system diagram depicting an embodiment of a cardiac monitoring device in communication with a plurality of other systems.

A cardiac monitoring device, such as the cardiac monitoring device 100 described above, may be useful in a plurality of situations. In some embodiments, such a cardiac monitoring device may be useful as a standalone device that, for example, performs all monitoring, detection, processing, therapy, and/or issue notification functions as a standalone unit or system. However, in various embodiments it can be desirable to connect the cardiac monitoring device 100 to one or more external devices or systems to, among other things, increase convenience, increase operating efficiency, enable notifications to be sent to third parties, enable external processing by systems that may be more efficient and/or may have access to relevant data the cardiac monitoring device does not have access to, and/or the like. FIG. 2 illustrates such an embodiment of a system where the cardiac monitoring device 100 is configured to electronically communicate with one or more other systems.

The system diagram of FIG. 2 comprises the cardiac monitoring device 100 configured to communicate directly or through a network 202 with a plurality of medical facilities 206, 207, and/or processing systems 204. For example, the cardiac monitoring device 100 may be configured to connect to, either wired or wirelessly, a computer system at medical facility 207 (or otherwise associated with a physician, medical facility, the patient, or other system) to transfer to that medical facility 207's computer system logged data that has been logged for a period of time while the patient or user was wearing the cardiac monitoring device 100. Such an embodiment may be useful to, for example, enable a physician (or even the user himself or herself) to review the logged data. In some embodiments, the logged data is transferred directly to the system at the medical facility, and in other embodiments, the logged data is transmitted to some other third-party and then transmitted to the medical facility. In some embodiments, as mentioned above, the cardiac monitoring device 100 may transfer raw logged data and/or may transfer data generated as a result of at least some processing or filtering of that raw data, such as to detect atypicalities.

Another use of the cardiac monitoring device 100 in a larger system as illustrated in FIG. 2 is the issuance of notifications and/or external processing of logged data or detected atypical cardiac sequences. For example, the cardiac monitoring device 100 can be configured to transmit through the network 202 to an external processing system 204 raw logged ECG data and/or detected atypical cardiac sequences from that logged data. In some embodiments, the cardiac monitoring device 100 is configured to transmit raw data to an external system. However, it can be desirable in some embodiments, such as to conserve bandwidth, to enable the cardiac monitoring device 100 to perform at least some initial processing and/or filtering on the logged data such that a smaller amount of data can be transmitted to the external processing system 204. Depending on the number and placement of electrodes, the device 100 can be configured for telemetry monitoring or a 12-lead ECG, for example. In some embodiments, the device 100 can be configured to take a signal-averaged ECG.

In this embodiment, the external processing system 204 can be configured to analyze those detected atypical cardiac sequences and make a determination as to whether the atypical cardiac sequence or sequences are relevant or important or a potential issue. For example, some detected atypical cardiac sequences may simply be atypical but may not be indicative of cardiac disease. However, other atypical sequences may be indicative of potential cardiac disease. If the processing system 204 determines that one or more atypical cardiac sequences are indicative of potential cardiac disease, the processing system 204 can be configured to issue one or more notifications, optionally including with those notifications data representing and/or explaining the sequence at issue. In some embodiments, such a notification can be transmitted from the processing system 204 through the network 202 to the medical facility 206. In some embodiments, such a notification can also be transmitted back through the network 202 to the cardiac monitoring device 100, such as to enable the cardiac monitoring device 100 to issue an electronic visual or audio notification to the patient or the wearer. It should be clear to one of skill in the art that the examples illustrated in FIG. 2 are only a few examples of how a distributed cardiac monitoring system such as disclosed herein may operate. In some embodiments, the device 100 can include a therapeutic feedback component such that the device 100 can be integrated with, or configured to communicate with another diagnostic and/or therapeutic medical device, such as, for example, a pacemaker (e.g., to increase or decrease the patient's heart rate), an Automated Implantable Cardioverter-Defibrillator (e.g., to deliver an electric shock to the patient), a therapeutic agent pump (to deliver, stop delivering, increase the dose, decrease the dose, or switch administering one or more therapeutic agents to the patient, including but not limited to a pressor or an anti-arrhythmic), an invasive ventilator, a CPAP or BIPAP machine, and the like.

Cardiac Monitoring Device

Figure 3:
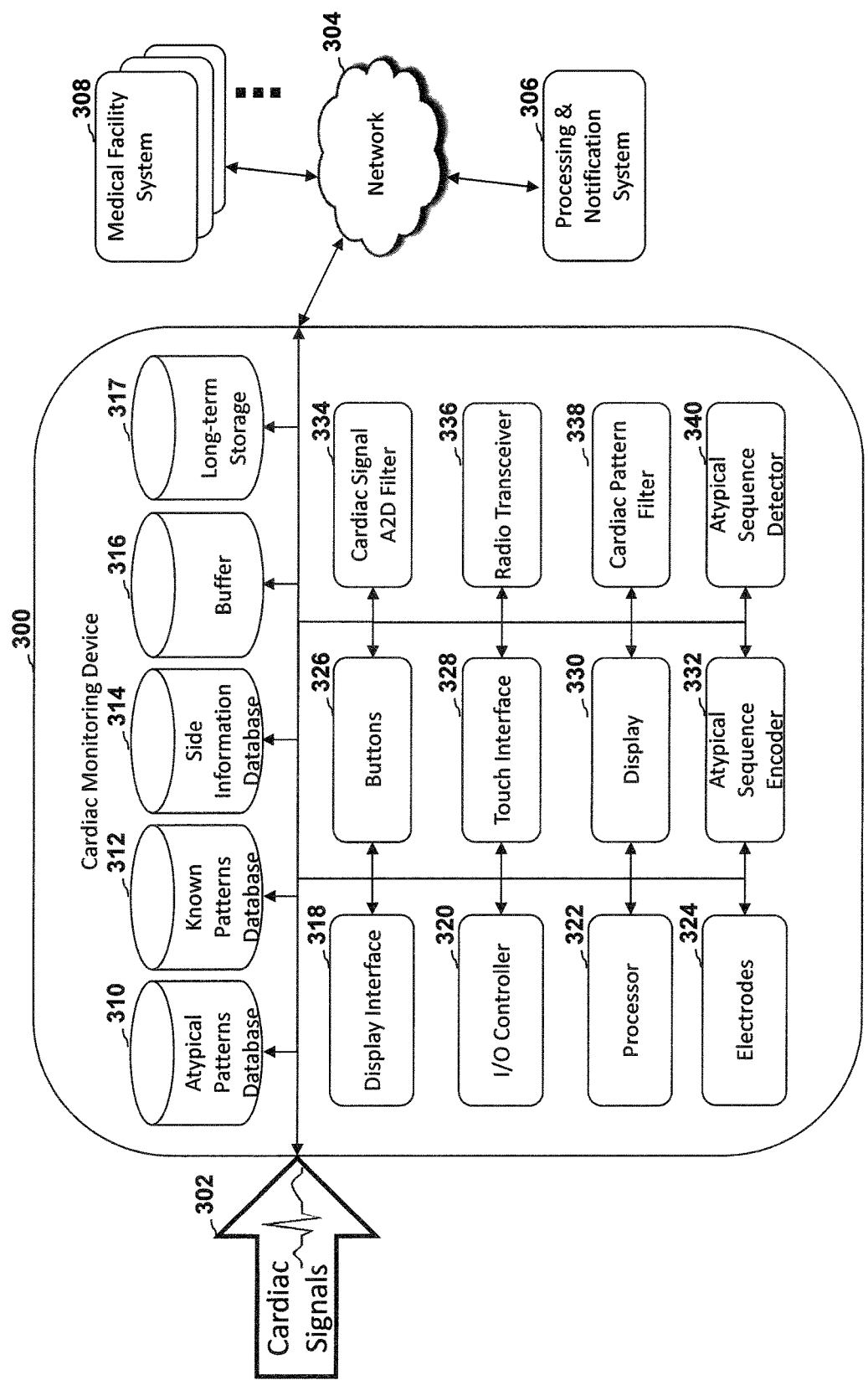
FIG. 3 is a block diagram of an embodiment of a cardiac monitoring device.

FIG. 3 illustrates an embodiment of a block diagram of another cardiac monitoring system utilizing concepts disclosed herein. In this embodiment, a cardiac monitoring device 300 is configured to detect cardiac signals 302, log and/or process those signals, and communicate through a network 304 with one or more medical facilities 308 and/or processing and notification systems 306. The system illustrated in FIG. 3 is somewhat similar to the system illustrated in FIG. 2, but with additional internal function detail shown for the cardiac monitoring device 300. The cardiac monitoring device 300 may be similar to the cardiac monitoring device 100 discussed above (e.g., a wearable watch-type device). Alternatively, the cardiac monitoring device 300 may take another form, such as a headband, chest band, ankle bracelet, pocket device, and/or the like.

The cardiac monitoring device 300 comprises a plurality of databases and other functional components. For example, the cardiac monitoring device 300 comprises an atypical patterns database 310, a known patterns database 312, a side information database 314, a buffer 316, and a long-term storage 317. The atypical patterns database 310 may, for example, be configured to store data relating to atypical patterns that have been detected in logged cardiac signals. The known patterns database 312 can be configured to, for example, store cardiac signal patterns that are currently known, such as patterns that are known to be indicative of cardiac disease, some of which are listed elsewhere herein (or known to not be indicative of cardiac disease). As discussed above, and some embodiments, an atypical pattern may be converted to a known pattern once that atypical pattern has been processed and determined to be an indicator of cardiac disease. Further, once an atypical pattern has been processed and determined not to be an indicator of cardiac disease, such pattern may also be stored as a known pattern, such as to enable the system to not flag such a pattern in the future. Such a feedback mechanism, as further described below, can be desirable to, among other things, reduce false positives when analyzing cardiac signals for atypical patterns that are potentially indicative of cardiac disease.

The side information database 314 can be configured to, for example, store data or information that can be used in conjunction with the cardiac signals 302 in, for example, determining whether a detected atypical pattern is a potential indicator of cardiac disease. For example, the side information database 314 may comprise information that helps the system to determine that a particular flagged atypical segment or sequence is not a potential indicator of cardiac disease for some reason indicated in the side information that is not based on this specific set of cardiac signals 302. The buffer 316 can be configured to, for example, be a temporary storage location, such as to temporarily store raw cardiac signals until they are processed and/or compressed. The long-term storage database 317 can be configured to store data over a longer period of time. For example, the long-term storage database 317 may be configured to store logged cardiac signals and/or detected atypical sequences or segments for eventual transmission to a physician's system (or other system) to enable the physician (or other user) to review or analyze such data.

Cardiac monitoring device 300 further comprises a display interface 318, an input/output controller 320, a processor 322, electrodes 324, buttons 326, a touch interface 328, a display 330, an atypical sequence encoder 322, a cardiac signal analog-to-digital filter 334, a radio transceiver 336, a cardiac pattern filter 338, and an atypical sequence detector 340. In various embodiments, a cardiac monitoring device may comprise less functional components or more or different functional components. One of skill in the art will recognize that the cardiac monitoring device 300 illustrated in FIG. 3 is merely one example embodiment of how techniques disclosed in here herein may be implemented.

The display interface 318 may, for example, be configured to control the display 330 to visually display notifications, messages, a graphical user interface, and/or the like to a user. The touch interface 328 may, for example, be configured to receive information from, for example, a digitizer that is positioned over or adjacent to the display 330 to receive touch-based input, such as a user placing his or her finger on the display 330. The I/O controller 320 can be configured to, for example, receive inputs from, for example, the buttons 326 or the electrodes 324, and/or to control outputs, such as to generate alerts or transmit other information through LEDs, a speaker, through the radio transceiver 336, and/or the like. The processor 322 can be configured to perform various computing tasks as required by the cardiac monitoring device 300, and/or may be configured to control various other functions of the device. Further, in some embodiments, the various functional components of the cardiac monitoring device may comprise discrete hardware components (e.g., integrated circuits and the like). However, in some embodiments, one or more of the functional components of the cardiac monitoring device 300 may be implemented in computer software as run by one or more computer processors.

The electrodes 324 can be configured to contact a user's skin and detect electrical signals from the user. The electrical signals can in some embodiments be passed to the cardiac signal analog-to-digital filter 334 that can be configured to convert those analog electrical signals to digital bits and store those digital bits in the buffer 316 and/or long-term storage 317 for processing.

The atypical sequence encoder 332 can be configured to encode cardiac signal data using various methods. For example, as will be further described below, the atypical sequence encoder 332 can be configured to encode a specific segment of data two (or sometimes more) times, the first time using a typical encoder (e.g., an arithmetic encoder), and the second time using a universal encoder (e.g., a universal source coder). The atypical sequence detector 340 can then be configured to compare the encoded bit lengths of these two encodings and determine whether the encoded bit length using the universal encoder is shorter than the encoded bit length using the typical or traditional encoder. In some embodiments, the definition of an atypical sequence is a sequence which can be encoded more efficiently, meaning using fewer bits, using a universal encoder as compared to a typical encoder. Accordingly, the atypical sequence detector 340 can be configured to detect an atypical sequence by determining that the encoded bit length using a universal encoder is shorter than the encoded bit length using a typical encoder. Further detail is given below of various examples of using typical and universal encoders.

The cardiac pattern filter 338 can be configured to, in some embodiments, for example, examine segments that have been determined to be atypical, and compare them to known patterns, such as those stored in the known pattern's database 312. Accordingly, the cardiac pattern filter 338 can be configured to filter out atypical patterns that turn out to already be known patterns, whether they are known to be irrelevant or to be a potential indicator of cardiac disease. In some embodiments, the cardiac pattern filter 338 can be configured to analyze the logged cardiac signal data before that data is even encoded or processed to detect atypicalities. One advantage of such a process may be to enable more efficient operation, because the typical and universal encoders may not need to be utilized on sections of data that are determined to already contain known patterns.

Cardiac Activity Atypical Pattern Detection

Figure 4:
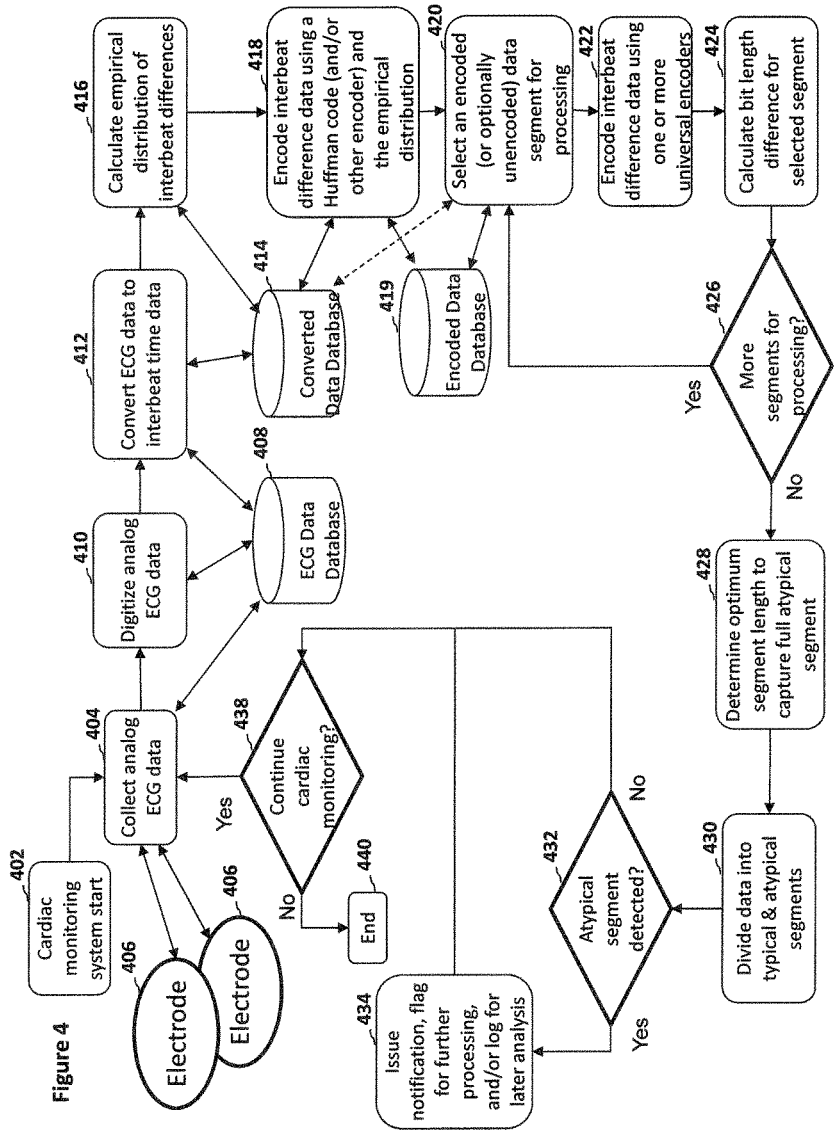
FIG. 4 is an embodiment of a process flow diagram depicting an example of detecting atypical cardiac signals.

FIG. 4 illustrates an example embodiment of a process flow diagram of detecting atypical cardiac activity. The process flow illustrated in FIG. 4 may be implemented by, for example, any of the cardiac monitoring systems disclosed herein, such as, for example, the cardiac monitoring device 300 illustrated in FIG. 3. The process flow begins at block 402. At block 404, the system collects analog electrocardiogram data. For example, the cardiac monitoring device 300 may utilize its electrodes 324 to collect the cardiac signals 302. In the process flow diagram of FIG. 4, the electrodes are represented by electrodes 406.

At block 410, the analog electrocardiogram data is digitized, such as, by, for example, the cardiac signal analog-to-digital filter 334 illustrated in FIG. 3. The digitized electrocardiogram data may be stored in the ECG data database 408, which may be part of, for example, the buffer 316 and/or long-term storage 317 of the cardiac monitoring device 300. At block 412, the system is configured to convert the electrocardiogram data to interbeat time data. This converted data is stored in the converted data database 414, which may also be part of, for example, the buffer 316 and/or the long-term storage 317 of the cardiac monitoring device 300. One benefit to converting the electrocardiogram data to interbeat time data is that the data is essentially compressed such that it represents similar information to the raw electrocardiogram data but using a smaller amount of storage or a smaller number of digital bits. In situations like this, where a relatively large amount of data is collected, it can be desirable to convert that data in some way such that the data is compressed and it thus can be more efficiently processed by a processing system. In this case, for example, the raw ECG data is converted or compressed by calculating the time between each heartbeat and representing the ECG data by a string of data comprising these times. For example, in its most basic sense, a typical heartbeat ECG trace comprises a plurality of peak spikes separated by relatively long periods of time with lower activity. Representing the entire trace, meaning both the peak spikes and the relatively long period of time in between the peaks, can take up a relatively large amount of data storage space. However, if the time between heartbeats (e.g., between peaks) is an interesting feature, the data can be significantly compressed, without losing relevant information, by encoding or converting the data with representations of the amount of time between each heartbeat.

Figure 5:
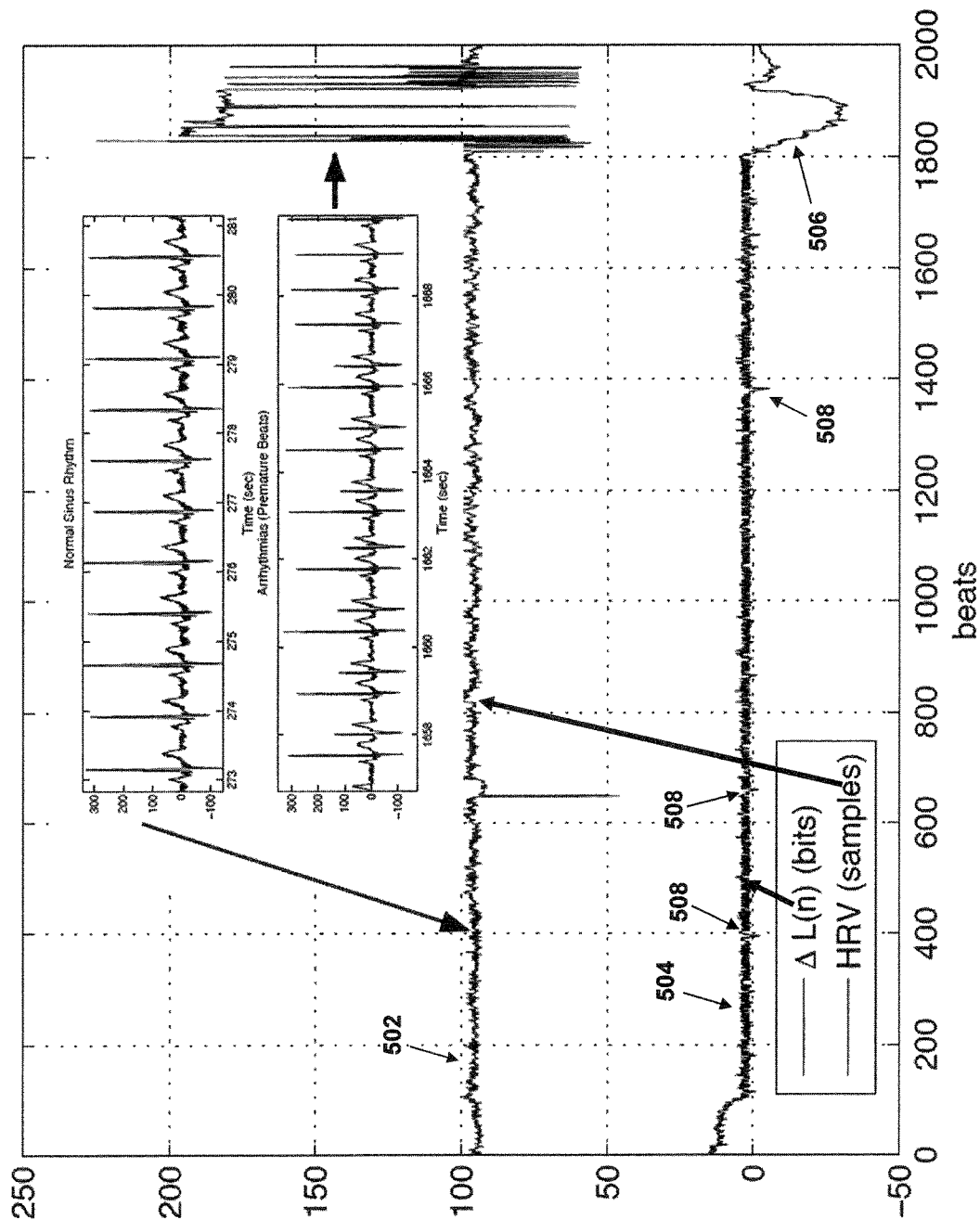
FIG. 5 is an embodiment of a graph showing an example result of performing the process flow of FIG. 4.

In some embodiments, the data can be even further compressed or converted by converting the raw inter-beat time intervals into inter-beat time interval differences. For example, if an average amount of time between heartbeats in a specific case is represented by approximately 950 milliseconds, each inter-beat time interval can be encoded as a particular number of milliseconds above or below that average time. Accordingly, each inter-beat time difference can be a relatively or very small number that can be encoded using a very or relatively small number of data bits. With reference to FIG. 5, which will be described in greater detail below, it can be seen that in this example, the inter-beat times averaged somewhere around 950 ms. However, most of the samples were within about 50 ms of that average. Accordingly, one way to convert or compress the ECG data would be to encode the raw inter-beat time, which would be somewhere around 950 ms. However, a second way to encode the data, which further compresses the data but represents similar information, would be to encode each inter-beat time interval as a difference from the average of about 950 ms. In this case, it can be seen that most of the inter-beat times could be encoded as a number no larger than about 50. This would take significantly fewer data bits and storage space than encoding each interval as the raw time.

At block 416, the system is configured to calculate an empirical distribution of the inter-beat differences. At block 418, the system is configured to encode these inter-beat differences a first time using a Huffman code in combination with the empirical distribution. It should be noted that various types of encoders may be utilized in this first encoding. A Huffman code (including an adaptive, canonical, or modified Huffman code) is not the only type of encoder that can be used. Various typical and/or universal encoders may be utilized, as will be described in further detail below. In some embodiments, one or more of a Unary, Golomb, Range, Shannon, Shannon-Fano, Shannon-Fano-Elias, Tunstall, or arithmetic encoder can be used. In some embodiments, one or more of an Exp-Golomb, Fibonacci, Gamma, or Levenshtein encoder can be used. Note also that in some embodiments, the data does not have to be actually encoded, but rather the system merely determines what the encoded bit length would be if the data were to be encoded. For example, the system may encode the data to determine the encoded bit length, but the system may choose to not store the encoded data but rather just store the length of the encoded data (which can take significantly less storage space than storing the encoded data itself). Accordingly, as shown in FIG. 4, the encoded data may be in some embodiments stored in the encoded data database 419. However, in some embodiments, the system is configured to store the length of the data if it were to be encoded but not necessarily the actual encoded data in the database 419.

A block 420, the system is configured to select an encoded data segment for processing. In some embodiments, particularly when the encoded data has not actually been stored, the system can be configured to select an unencoded data segment for processing (e.g., from database 408 or 414 instead of 419). At block 422, the system is configured to perform a second encoding (or encoded length determination) by encoding inter-beat difference data using one or more universal encoders. Various universal encoders may be utilized, as will be described in further detail below. In some embodiments, for example, a Lempel-Ziv (LZ77 or LZ78), a Context Tree Weighting (CTW), a Burrows-Wheeler transform based coder, partial predictive mapping (PPM) based coder, and/or an encoder based on T-complexity can be used.

In this example, this is the second time that the segment of data will have been encoded, except now the segment is encoded using a different encoder (or potentially the same or similar encoded, but the encoder being untrained), in this case specifically a universal encoder, as is described in more detail below.

At block 424, the system calculates a bit length difference for the selected segment. For example, the system can be configured to compare the encoded length of the data using the typical or other encoder from block 418 to the encoded length from block 422 (e.g., subtract the encoded length of the data using the typical or other encoder of block 418 from the encoded length of block 422, or vice versa). The significance of this comparison is that, if the encoded length from block 422, the encoded length from the universal encoder, is shorter than the encoded length from block 418 (e.g., subtracting the encoded length of block 418 from the encoded length of block 422 results in a negative number), then an atypical segment has likely been detected. On the other hand, if the encoded length from block 422 is longer than the encoded length from block 418, the segment is likely not atypical, or at least the segment is not detectable as being atypical using the specific encoders that were used.

At block 426, the process flow varies depending on whether there are more data segments to process. As long as there are more data segments to process, the process flow proceeds back to block 420 and proceeds as described above. When there are no more segments for processing, or in some cases operating in parallel to the process flow of blocks 420 through 426, the process flow proceeds to block 428. At block 428, the system determines the optimum segment length to capture a full atypical segment. For example, if the system determined at block 424 that the universal encoded length was shorter than the encoded length from block 418, then the system knows that an atypical segment is present. However, just looking at this difference in encoded length may not be enough information to know whether the entire atypical segment has been captured. For example, the atypical segment may be a subsegment of the encoded segments, or the encoded segment may comprise a subsegment of the true full atypical segment. Accordingly, at block 428, the system can be configured to basically repeat the prior blocks, but with different segment lengths or subsections of segments until the full atypical segment is captured.

At block 430, the data is divided into typical and atypical segments. At block 432, the process flow varies depending on whether an atypical segment has been detected. If an atypical segment has been detected, the process flow proceeds to block 434. At block 434, various actions can occur. For example, a notification can be issued, such as to the user or wearer, the user's physician, and/or the like that a potential issue has been detected. However, as will be discussed in greater detail below, just because an atypical segment has been detected, this does not necessarily mean that the atypical segment is an indicator of cardiac disease. The atypical segment could represent artifact caused by patient motion, for example. Accordingly, in some embodiments, instead of or prior to issuing a notification, the system may be configured to flag that atypical segment for further processing and/or log that segment for later analysis. Once that segment has been processed, either automatically by the system or another system, or by review of a physician, and the segment has been determined to be indicative of potential cardiac disease, then a notification or other action may take place. The process flow then proceeds to block 438.

At block 438, the process flow varies depending on whether cardiac monitoring should be continued. If cardiac monitoring should be continued, the process flow proceeds back to block 404 and proceeds as described above. If cardiac monitoring is complete, such as, for example, the user has indicated that he or she does not wish to monitor his or her cardiac activity anymore, the process flow proceeds to block 440, and the process flow is complete.

FIG. 5 illustrates an example of a cardiac monitoring and analysis session performed by, for example, the process flow of FIG. 4, as described above. The graph in FIG. 5 comprises two lines or traces, namely, a heart rate variability (HRV) line 502, and an encoded bit length difference trace 504. For example, the trace 502 is depicting inter-beat times, such as from the converted data at block 412 of FIG. 4. The trace 504 is depicting the difference in encoded lengths between the processes of block 418 and 422 of FIG. 4. Specifically, the difference depicted by trace 504 represents the calculation of block 424 of FIG. 4.

Since one definition as disclosed herein of an atypical segment of data is any time the encoded length using a universal encoder is shorter than the encoded length using a typical encoder, any time the trace 504 drops below zero, an atypical segment has potentially been detected. As can be seen at the right end of the graph, section 506 drops well below zero and is thus an indicator of an atypical segment of this ECG data. This atypical segment can be visually confirmed by reviewing the inter-beat time trace 502 at the same right end. It can be seen that an arrhythmia occurred at this section and the inter-beat times varied vastly more than normal. It should be noted that an important distinction to make here is that the process flow used to generate this data is not necessarily looking for variations in inter-beat times. The process flow rather is looking for any atypicality in the data.

Although the process flow of FIG. 4 is clearly able to detect this significant variation in inter-beat times, the process can also detect various other atypicalities, even atypicalities that may not be visually apparent by looking at the trace 502. For example, it can be seen in trace 504 that there are several other sections where the trace 504 dips below zero. A few of these spots are indicated by the reference number 508. These dips below zero are not nearly as significant as the dip below at reference number 506. This does not necessarily mean that the locations 508 are not indicative of atypical sequences, and potentially may be indicators of an atypical sequence that has something to do with another characteristic of the heartbeat that is not related to inter-beat times. ECG is considered as a non stationary process. Its mean value and its standard deviation vary over the time. However, it contains useful information that can be interpreted as a pseudo deterministic pattern, referred to as a PQRST pattern. During each heartbeat a healthy heart will have an orderly progression of a wave of depolarization that is triggered by the cells in the sinoatrial node, spreads out through the atrium, passes through intrinsic conduction pathways and then spreads all over the ventricles. The normal ECG includes a P wave, a QRS complex and a T wave. The P wave represents atrial depolarization and the QRS represents ventricular depolarization. The T wave reflects the phase of rapid repolarization of the ventricles.

There are several abnormalities that may be noted when a PQRST wave is analyzed. They may include one or more of the following: Inversion in leads where the P is normally upright or the presence of an upright P wave in AVR. This change is often found in conditions where the impulse travels through the atria via an abnormal pathway, such as ectopic atrial or A-V nodal rhythms; Increased Amplitude usually indicates atrial hypertrophy and is found especially in A-V valvular disease, hypertension, cor pulmonale, and congenital heart disease; Decreased Amplitude may indicate chronic obstructive pulmonary disease or pericardial tamponade; Increased Width often indicates left atrial enlargement or diseased atrial muscle; Biphasity is a notable sign of left atrial enlargement when the second half of the P wave is significantly negative in leads III and V1; Notching In P-Mitrale: the P often is wide and notched and is taller in lead I than in lead III. Notching is considered significant when the distance between peaks is greater than 0.04 seconds; Peaking indicates right atrial strain. These tall pointed P waves are often taller in lead III than in lead I. This is known as P-Pulmonale; Absence of P waves occurs in A-V nodal rhythms and S-A Block; abnormalities in the length of the PR, QRS, QT, QTc intervals; ST elevations (which could be indicative of a myocardial infarction or pericarditis); or ST depressions (which could be indicative of cardiac ischemia). In some embodiments, the device could be configured to determine atypical patterns using one, two, or more of the aforementioned variables, or others. In some embodiments, the device could be configured to diagnose the presence of, or a future risk of sudden cardiac death, myocardial infarction, atrial tachycardia, atrial flutter, ventricular tachycardia, ventricular fibrillation, atrial fibrillation, Mobitz type 1 or type 2 block, complete heart block, sick sinus syndrome, congestive heart failure, valvular stenosis or regurgitation (including diseases of the mitral or aortic valves), cardiac ischemia, stroke, pulmonary embolism, Wolff-Parkinson-White syndrome, sudden infant death syndrome, or other known or unknown conditions.

In some embodiments, it can be desirable to only review and process the most significant atypicalities. For example, the system may be configured to process and interpret every single time the trace 504 dips below zero in some embodiments. However, doing so may take significant resources and may lead to marginal or marginally useful information, particularly for small or relatively small dips below zero. Further, some relatively small dips below zero may merely be noise in the data and may not necessarily be indicative of a true atypical situation. Accordingly, for all these reasons, in some embodiments, the system can be configured to utilize a threshold that must be exceeded for the system to pay attention to or process a particular potential atypical sequence. For example, in this case, if the threshold were, for example, −10, the only portion of the trace 504 that would trigger this or exceed this threshold would be the section 506. In some embodiments, the threshold is set as a predetermined value. However, in other embodiments, the threshold can be a dynamic number that is dynamically adjusted to the current data being analyzed, such as to limit a number of detected atypicalities to only the most significant atypicalities. In some embodiments, the system can be configured to have a certain tolerance threshold, that is, flag only segments or sub-segments having an encoded length that is below about or at least about 1%, 2%, 3%, 4%, 5%, 6%, 7%, 8%, 9%, 10%, 12%, 15%, 20%, 25%, 30%, 35%, 40%, 45%, 50%, or more with respect to a typical encoded length.

Figure 6:
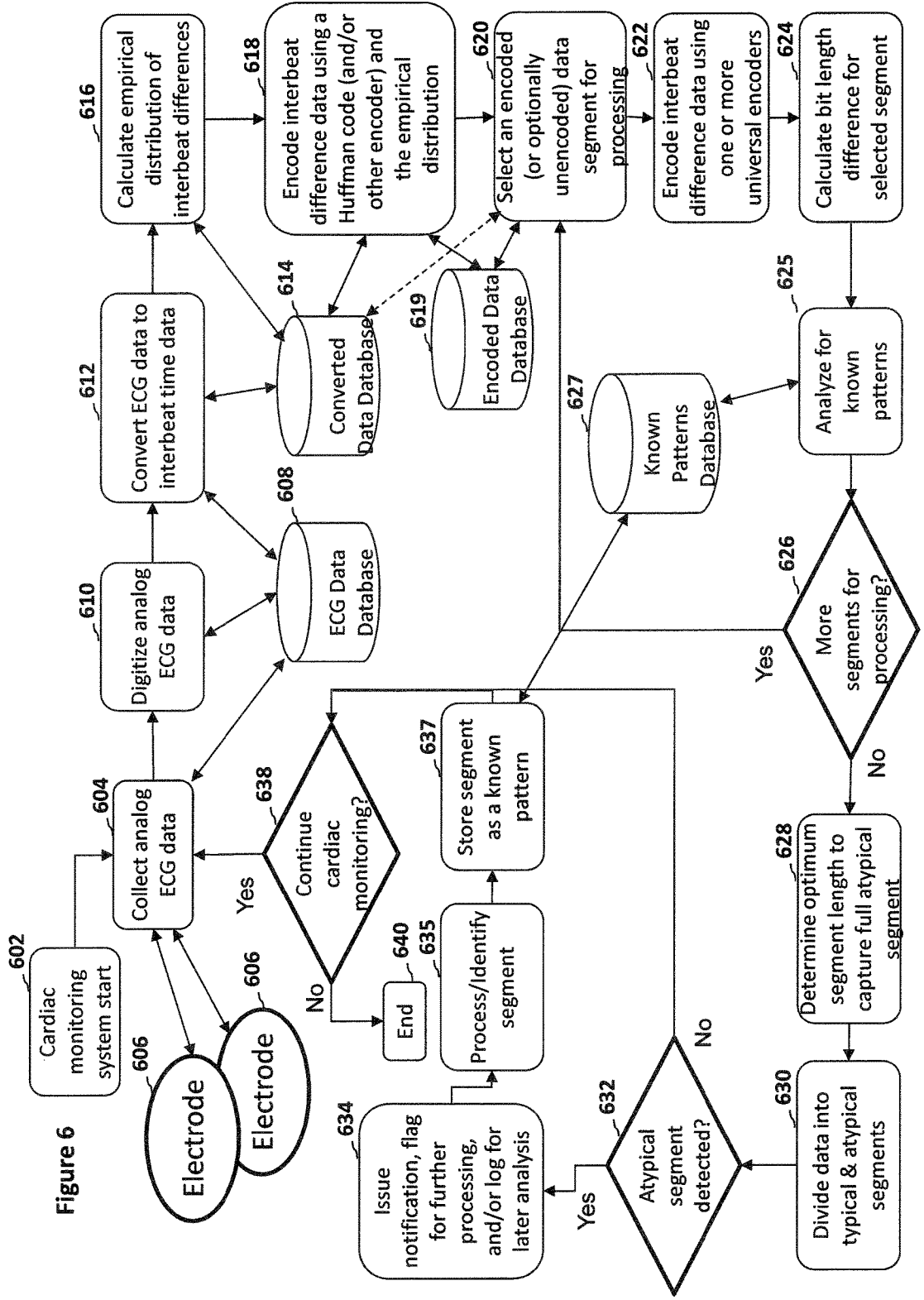
FIG. 6 is another embodiment of a process flow diagram depicting an example of detecting atypical segments in cardiac activity.

FIG. 6 illustrates an alternative embodiment of a process flow diagram of a process for monitoring electrocardiogram data for atypicalities. The process flow illustrated in FIG. 6 is similar to the process flow illustrated in FIG. 4, as discussed above. One difference in the process flow of FIG. 6 is that the process flow of FIG. 6 analyzes data for indications of known patterns, such as to increase efficiency by not flagging atypical patterns for later analysis if such atypical pattern is actually already a known pattern. Further, this process incorporates a feedback mechanism so that, once an atypical pattern has been identified, that atypical pattern can be entered into the known patterns database to make the process a learning process and an intelligent process. Accordingly, as more and more ECG data is monitored and processed, the system can become smarter and thus potentially produce fewer false alarms and more efficiently detect true issues of potential cardiac disease.

The process flow begins at block 602. At block 604, the system collects analog electrocardiogram data, such as, for example from the electrodes 606. At block 610, the ECG data is digitized and stored in the ECG data database 608. At block 612, the ECG data is converted to inter-beat time data, or in some embodiments, converted otherwise or left in a raw state. At block 616, an empirical distribution of the inter-beat differences is calculated. At block 618, the inter-beat difference data is encoded using a first encoder, such as a typical encoder (e.g., a Huffman code and/or other encoder). In some embodiments, this encoding is used in conjunction with the empirical distribution calculated at block 616. In some embodiments, the empirical distribution is not utilized and thus the compilation of the empirical description at block 616 is optional.

At block 620, the system selects an encoded or optionally unencoded data segment for processing. It should be noted that the order of blocks in this process flow diagram (and various other process flow diagrams discussed herein) may be different than as shown here. For example, in some embodiments, the selection of a segment for processing may be before the first encoding, such as before block 618. At block 622, the system encodes the inter-beat difference data using one or more universal encoders, such as encoders different in some way than the encoder used at block 618. At block 624, the system calculates a bit length difference for the selected segment between the two encodings. As discussed above, if the second encoding using the one or more universal encoders is shorter than the first encoding, this is an indication that an atypical segment has likely been detected. In some embodiments, the system is configured to individually compare each universally encoded length to the first encoding, since some universal encoders may detect an atypical sequence on some data, while others may not.

As discussed above, even though the process flow illustrated in FIG. 6 comprises actually encoding the inter-beat difference data using two or more encoders, in some embodiments, the system may be configured to merely calculate the length of the encoded data if it were to be encoded with these encoders, rather than actually encoding and storing that encoded data.

At block 625, the data is analyzed for known patterns. For example, the system can be configured to consult the known patterns database shown at block 627 to determine if the data in the selected segment comprises or is a portion of a known pattern. If the segment is related to a known pattern, the system can be configured to act accordingly. For example, if the system already knows that such a pattern is a potential indicator of cardiac disease, the system can be configured to act appropriately, such as by issuing a notification. Further, if the system knows that this known pattern is innocuous or irrelevant or not indicative of cardiac disease or other issues, the system can be configured to ignore this segment and proceed on in the process flow.

At block 626, the process flow varies depending on whether there are additional segments for processing. If there are additional segments for processing, the process flow proceeds back to block 620 and proceeds as described above. If there are no additional segments for processing, the process flow proceeds to block 628. At block 628, the system determines an optimum segment length to capture a full atypical segment, as discussed above. At block 630, the data is divided into typical and atypical segments. This is assuming that one or more atypical segments were found. At block 632, the process flow varies depending on whether an atypical segment has been detected. If an atypical segment has not been detected, the process flow can proceed to block 638, where the process flow ends at block 640. If cardiac monitoring is not to be continued, the process flow proceeds back to block 604 and cardiac monitoring is continued.

If an atypical segment has been detected, the process flow proceeds from block 632 to block 634. At block 634, the system can be configured to, for example, issue a notification, flag this segment for further processing, and/or log this segment for later analysis. At block 635, the flagged or atypical segment is processed and/or identified. For example, the system itself may process or identify the segment, or the system may send this segment to a third-party system or individual for identification or processing. Once the atypical segment has been processed or identified, the system can be configured to store that segment as a known pattern at block 637. Accordingly, this atypical segment is now a known pattern added to the known patterns database 627, to enable more efficient future processing. The process flow then proceeds to block 638 as described above.

Atypical Data Detection System

The systems and techniques disclosed herein have other uses in the realm of monitoring and diagnosing cardiac disease, potentially saving millions of lives. However, the techniques disclosed herein also have implications in a plurality of potential other applications. For example, systems and techniques as disclosed herein for detection of atypical data may be used for detection of other human diseases, analyzing genetic information for detection of potential issues, and/or the like. Further, such techniques may be utilized in fraud and crime detection and prevention. For example, such techniques may be utilized in the cybersecurity context, for example, to detect cyber-attacks of computer networks, or utilized for detecting insider trading, credit card fraud, illicit art deals, terrorism, piracy, monitoring of vast amounts of electronic (digital or analog) indications, video surveillance, monitoring of computer network searches in Internet search engines, auditing financial data, and/or the like. Further, the techniques disclosed herein may have a plurality of uses in analyzing large datasets to determine atypical or interesting data in such datasets. For example, the techniques disclosed herein may be useful in analyzing stocks, vast amounts of textual materials, medical information for medical trials, image databases, medical research, climate research, environmental research, seismic research, genomics, scientific data, business data, and/or social networks. The techniques disclosed herein may also have applications in, for example, devices such as airplanes and cars or utility networks.

One of the desirable uses of the systems and techniques disclosed herein is that these techniques are able to identify "unknown unknowns." What we mean by this is that prior systems are intended to analyze information to look for things that we already know are indicators of interesting or important information. The techniques disclosed herein, on the other hand, are able to detect data or information that is potentially interesting or important, even if we presently have no idea that such types of data may be interesting or important. In some cases, the types of data detected by systems that are looking for known things may overlap with the types of things detected by the systems disclosed herein. However, the systems and techniques disclosed herein are able to additionally detect things that past systems are not able to test to detect, because no one knew that we wanted to detect such a piece of data.

Figure 7:
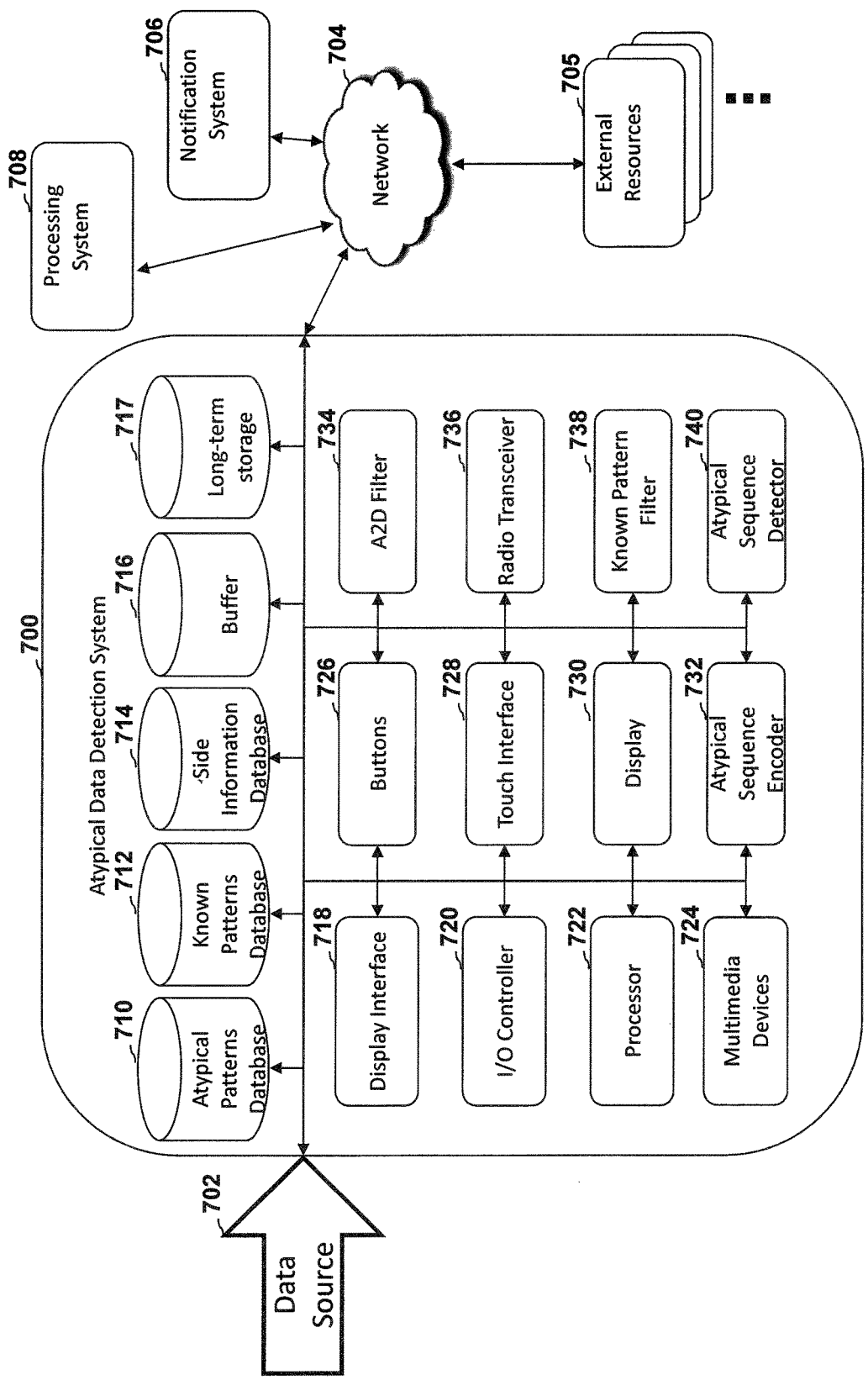
FIG. 7 is a block diagram of an embodiment of a system for detection of atypical data.

FIG. 7 illustrates an embodiment of an atypical data detection system 700 configured to receive data from a data source 702 and detect atypical sequences in that data. The system may be utilized in cardiac monitoring, as described above, or in any other situation where data is to be analyzed for atypical sequences, for example, in the cybersecurity context. In some embodiments, the atypical data detection system 700 is configured to communicate through one or more computer networks 704 with one or more external resources, such as the external resources 705, a notification system 706, and/or a processing system 708. The atypical data detection system 700 is in some ways similar to the cardiac monitoring system illustrated in FIG. 3, as discussed in detail above. Accordingly, similar reference numbers are used to indicate some features of the atypical data detection system 700 that are similar to features of the cardiac monitoring device 300 discussed above. Further, while FIG. 7 illustrates one embodiment of an atypical data detection 700 comprises a plurality of features, such as user interface features such as multimedia devices 724, button 726, a touch interface 728, the electronic display 730, and/or the like, various other embodiments may include more or fewer features. For example, some embodiments of an atypical data detection system may not have any direct user interface features. However, other embodiments may have even more user interface features. Further, some embodiments may be configured to generate a personalized user interface specific to a particular user, set of data, situation, and/or the like. This personalized user interface may be configured to, for example, enable a user to adjust settings of the system, review logged data, review and/or interpret detected atypical sequences, and/or the like.

The atypical data detection system 700 comprises a plurality of databases in this embodiment, including an atypical patterns database 710, a known patterns database 712, a side information database 714, a buffer 716, and a long-term storage 717. These databases are configured to operate similarly to the databases of the cardiac monitoring device 300. The additional features of the atypical data detection system 700 comprise a display interface 718, an input-output controller 720, a processor 722, an atypical sequence encoder 732, an analog-to-digital filter 734, a radio transceiver 736, a known pattern filter 738, and an atypical sequence detector 740. These features can also be configured to operate similarly to similar features of the cardiac monitoring device 300. Further, the atypical data detection system 700 can be configured to operate as will be discussed below with reference to, for example, the process flow diagrams of FIGS. 8 and 9.

Atypical Data Detection Processes

Atypical data can be detected in various ways as disclosed herein. For example, one method of detecting atypical data comprises calculating the code length of a sequence of data given a probability model of typical data, for example using an arithmetic coder, otherwise referred to herein sometimes as a typical encoder. Next, the method can calculate the code length of the same sequence using any universal source coder. The code lengths for these two encodings can then be compared, and if the encoded length using the universal encoder is shorter than the other encoded lengths, then atypical data has been detected. It should be noted that, although this embodiment describes calculating the code length using a single typical encoder and a single universal encoder, various other embodiments may utilize a plurality of encoders. For example, in one embodiment, the system may be configured to initially calculate an encoded length using a typical or arithmetic encoder, and then calculate encoded lengths using a plurality of individual universal encoders. The system can be then be configured to individually test the encoded lengths using each of the individual universal encoders versus the typical encoder. In some embodiments, some universal encoders may result in a lower encoded length than others. Accordingly, atypical data, particularly in some cases data that is not significantly atypical, or that may be atypical in a specific way, may be detectable using some universal encoders and not others. This is not always the case, however.

The example given above utilized a different encoder to perform the first encoding than the second or additional in encodings. However, in some embodiments, the same encoder may actually be used for both encodings, but the encoder may be set up differently during the two encodings. For example, a universal source coder may be trained on a particular set of data. That universal source coder may then be frozen after the initial training. Now a segment of data may be put through the frozen universal source coder to calculate a code length of that segment of data (e.g., the first encoding). Second, that segment of data may be put through the same universal encoder, but not frozen or potentially not even trained on the previous data (e.g., the second encoding). Now, the encoded lengths can be compared, and if the second encoded length is shorter than the first, atypical data has been detected.

Figure 8:
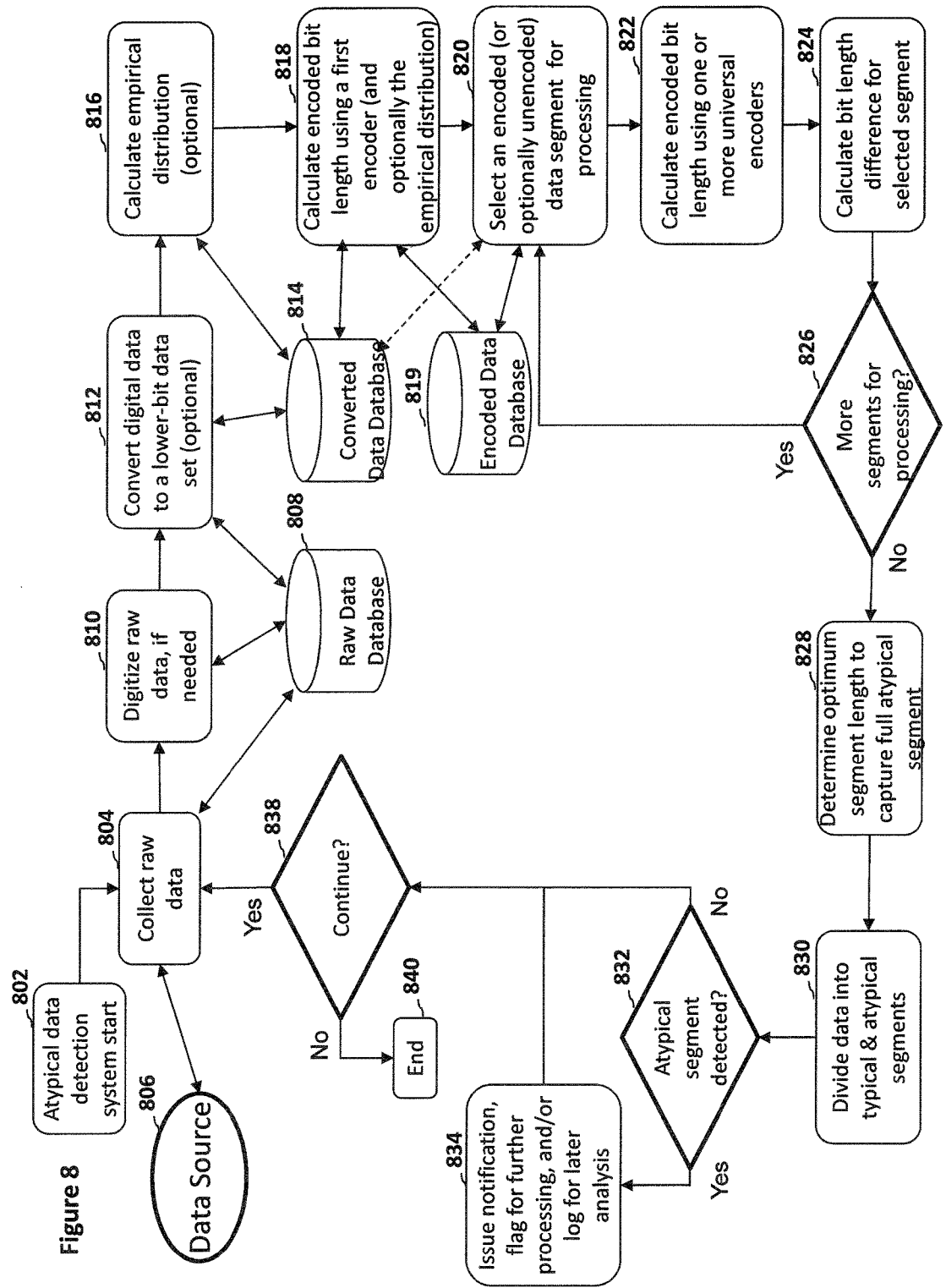
FIG. 8 is an embodiment of a process flow diagram depicting an example of detecting atypical data.

FIG. 8 illustrates an example embodiment of a process flow diagram comprising detection of atypical data. The process flow shown in FIG. 8 may be implemented by, for example, the atypical data detection system 700 of FIG. 7. The process flow begins at block 802. At block 804, raw data is collected from a data source 806. At block 810, the raw data is optionally digitized if needed. For example, if the raw data is analog data, such as electrocardiogram data from electrodes, that data may need to be digitized before it can be processed. However, in some embodiments, the raw data does not need to be digitized. Digitizing of raw data may be performed by, for example, the analog-to-digital filter 734 of the atypical data detection system 700.

At block 812, the data is optionally converted to a lower bit data set. Similarly to as described above with respect to the electrocardiogram example, it can be desirable in some embodiments to reduce the overall bit size of the data, to enable more efficient storage and processing of that data. This conversion may comprise, for example, lossless or lossy compression, conversion from one data type to another data type, and/or the like. However, in some embodiments, the data is not converted or compressed.

At block 816, in empirical distribution of the data is optionally calculated. In some embodiments, it can be desirable to have an empirical distribution, such as if a particular encoder being used is based on probability data. However, in other embodiments, an encoder may not require an empirical distribution, and an empirical distribution may not need to be calculated.

At block 818, the system calculates an encoded length using a first encoder. For example, a bit length of a particular segment of data may be calculated using a typical encoder, and/or a universal source coder that has been trained and frozen. At block 820, an encoded or optionally unencoded data segment is selected for processing. Similarly to as discussed above, this selection of a data segment for processing may in some embodiments occur before the first encoding of block 818.

At block 822, a second encoding occurs, and/or a second calculation of encoded bit length occurs, using one or more universal source coders. At block 824, the calculated bit length from block 822 is compared to the calculated bit length from block 818. As discussed above, if the calculated bit length from block 822 is shorter than the calculated bit length of block 818, then atypical data has likely been detected.

At block 816, the process flow varies depending on whether there are more segments for processing. If there are more segments for processing, the process flow proceeds back to block 820, and proceeds as discussed above. If there are not more segments for processing, (or optionally in parallel) the process flow proceeds to block 828. At block 828, the system determines an optimum segment length to capture a full atypical segment. For example, if it was determined at block 824 that an atypical segment has been detected, the system may be configured to vary iteratively the length of the segment to ensure (or increase the likelihood that) the full atypical segment has been captured.

At block 830, assuming atypical data has been detected, the data is divided into typical and atypical segments. At block 832, the process flow varies depending on whether an atypical segment has been detected. If an atypical segment has not been detected, the process flow proceeds to block 838 and either completes at block 840 or returns back to block 804 as discussed above. If an atypical segment has been detected, the process flow proceeds to block 834. At block 834, various actions can occur, such as issuing a notification that an atypical segment has been detected, flagging that segment for further processing and/or identification, and/or logging that detected segment for later review and analysis. The process flow then proceeds to block 838 and proceeds as described above.

Figure 9:
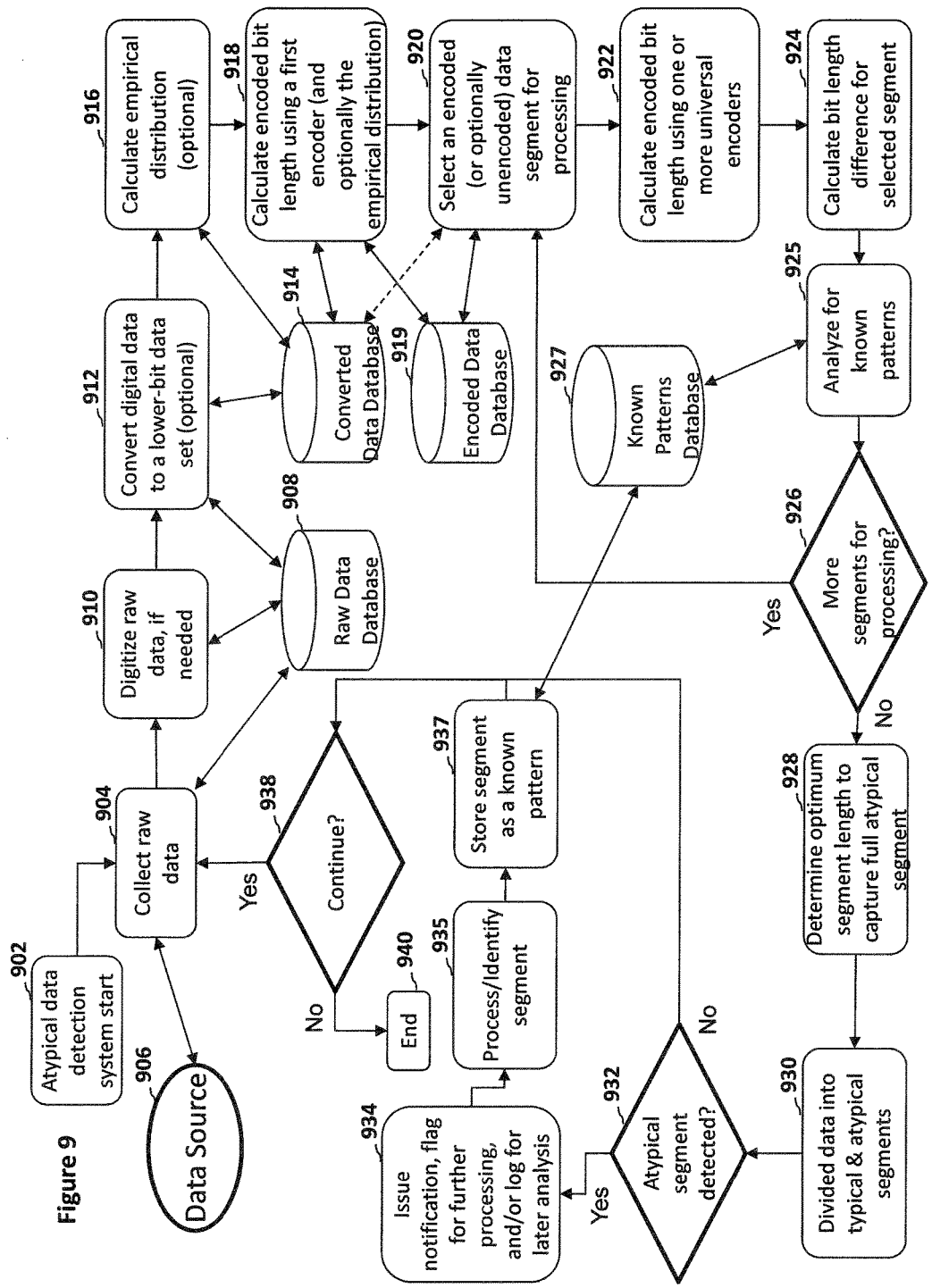
FIG. 9 is another embodiment of a process flow diagram depicting another example of detecting atypical data.

FIG. 9 illustrates another example embodiment of a process flow diagram illustrating a process flow for detecting atypical data from an input data source. The process flow illustrated in FIG. 9 may again be implemented by, for example, the system illustrated in FIG. 7. The process flow of FIG. 9 is similar to the process flow of FIG. 8. However, the process flow of FIG. 9 further incorporates analyzing data for known patterns and potentially implementing a feedback mechanism that incorporates detected atypical segments that have been processed or identified into that known pattern database.

The process flow begins at block 902. At block 904, the system collects raw data from a data source 906. At blocks 910 through 916, similarly to as described above, the raw data is digitized if needed, optionally converted to a lower bit data set, and potentially an empirical distribution is calculated. At block 918, a first encoded bit length is calculated using a first encoder, such as a typical or arithmetic encoder or a universal source coder that has been trained with a specific set of data and frozen. At block 920, a specific subset or segment of data is selected for processing. As discussed above, this block may occur before the first encoded bit length is calculated. At block 922, a second encoded bit length is calculated using one or more universal encoders. At block 924, a bit length difference is calculated between the first and second encoded bit length calculations. If the second encoded bit length is shorter than the first, then atypical data has likely been detected.

At block 925, the segment is analyzed for known patterns, such as known patterns stored in the known patterns database 927. Similarly to as discussed above, if a known pattern is present, this may make processing more efficient, because further processing on that segment may potentially not be needed, since its pattern is already recognized.

At block 926, the process flow varies depending on whether there are more segments for processing. If there are more segments for processing, the process flow proceeds back to block 920 and proceeds as described above. Otherwise, the process flow proceeds to block 928, and the optimum segment length to capture the full atypical segment is determined. At block 930, the data is divided into typical and atypical segments. At block 932, the process flow varies depending on whether an atypical segment was detected. If an atypical segment was detected, the process flow proceeds to block 934, and various things can happen. For example, a notification can be issued, the segment can be flagged for further processing, and/or logged for later analysis. At block 935, the segment can optionally be processed and/or identified. Once the segment has been identified, at block 937, that segment can be now stored as a known pattern in the known patterns database 927. This thus implements a feedback mechanism that enables the system to learn as it goes. The process flow then proceeds to block 938, and either ends at block 940 or continues by proceeding back to block 904 and proceeding as described above.

Computing System

Figure 10:
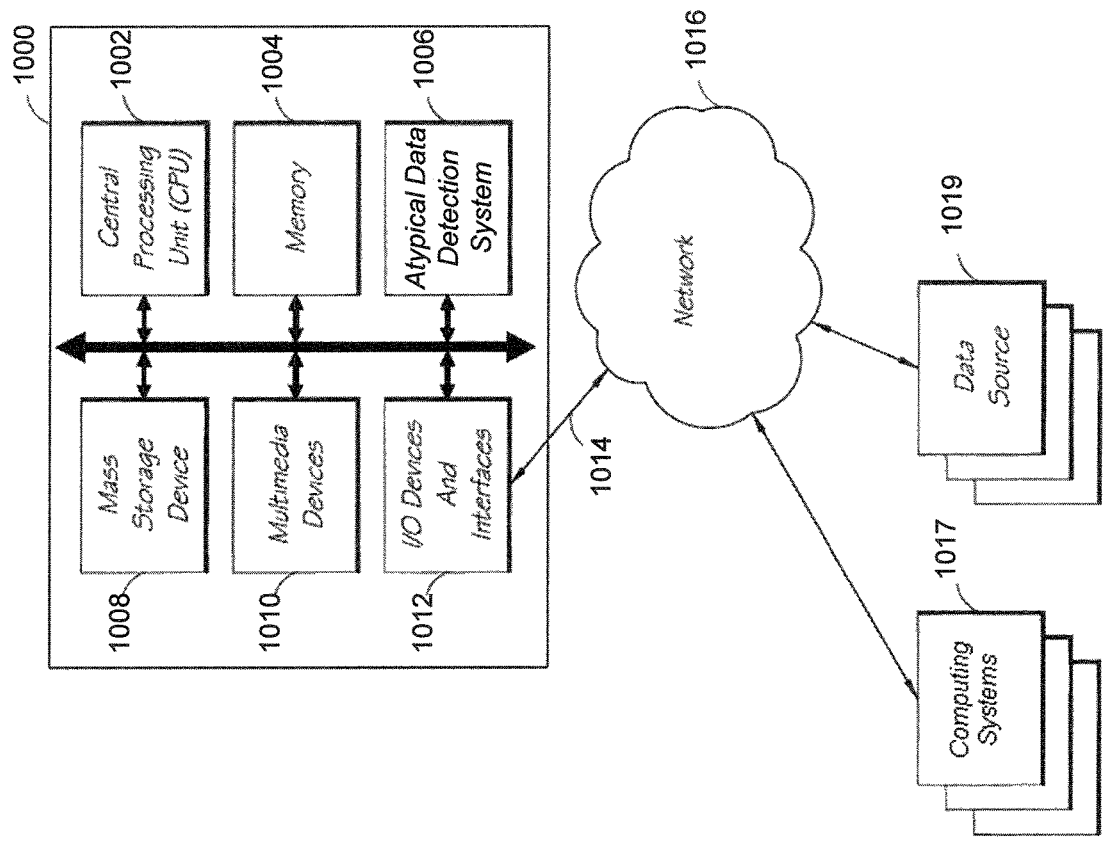
FIG. 10 is a block diagram depicting an embodiment of a computer hardware system configured to run software for implementing one or more embodiments of the systems described herein.

FIG. 10 is a block diagram depicting an embodiment of a computer hardware system configured to run software for implementing one or more embodiments of the atypical data detection systems described herein.

In some embodiments, the computer devices, clients, and/or servers described herein take the form of a computing system 1000 illustrated in FIG. 10 which is a block diagram of one embodiment of a computing system that is in communication with one or more computing systems 1017 and/or one or more data sources 1019 via one or more networks 1016. The computing system 1000 may be used to implement one or more of the systems and methods described herein. In addition, in one embodiment, the computing system 1000 may be configured to manage access or administer a software application. While FIG. 10 illustrates one embodiment of a computing system 1000, it is recognized that the functionality provided for in the components and modules of computing system 1000 may be combined into fewer components and modules or further separated into additional components and modules.

Atypical Data Detection System Module

In one embodiment, the computing system 1000 comprises an atypical data detection system module 1006 that carries out the functions described herein with reference to detecting and/or processing atypical data, including any one of the techniques described above. The atypical data detection system module 1006 and/or other modules or functional units disclosed herein may be executed on the computing system 1000 by a central processing unit 1002 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into submodules despite their physical organization or storage.

Computing System Components

In one embodiment, the computing system 1000 also comprises a mainframe computer suitable for controlling and/or communicating with large databases, performing high volume transaction processing, and generating reports from large databases. The computing system 1000 also comprises a central processing unit ("CPU") 1002, which may comprise a conventional microprocessor. The computing system 1000 further comprises a memory 1004, such as random access memory ("RAM") for temporary storage of information and/or a read only memory ("ROM") for permanent storage of information, and a mass storage device 1008, such as a hard drive, diskette, or optical media storage device. Typically, the modules of the computing system 1000 are connected to the computer using a standards based bus system. In different embodiments, the standards based bus system could be Peripheral Component Interconnect (PCI), Microchannel, SCSI, Industrial Standard Architecture (ISA), and Extended ISA (EISA) architectures, for example.

The computing system 1000 comprises one or more commonly available input/output (I/O) devices and interfaces 1012, such as a keyboard, mouse, touchpad, and printer. In one embodiment, the I/O devices and interfaces 1012 comprise one or more display devices, such as a monitor, that allows the visual presentation of data to a user. More particularly, a display device provides for the presentation of GUIs, application software data, and multimedia presentations, for example. In one or more embodiments, the I/O devices and interfaces 1012 comprise a microphone and/or motion sensor that allow a user to generate input to the computing system 1000 using sounds, voice, motion, gestures, or the like. In the embodiment of FIG. 10, the I/O devices and interfaces 1012 also provide a communications interface to various external devices. The computing system 1000 may also comprise one or more multimedia devices 1010, such as speakers, video cards, graphics accelerators, and microphones, for example.

Computing System Device/Operating System

The computing system 1000 may run on a variety of computing devices, such as, for example, a server, a Windows server, a Structure Query Language server, a Unix server, a personal computer, a mainframe computer, a laptop computer, a tablet computer, a cell phone, a smartphone, a personal digital assistant, a kiosk, an audio player, an e-reader device, and so forth. The computing system 1000 is generally controlled and coordinated by operating system software, such as z/OS, Windows 95, Windows 98, Windows NT, Windows 2000, Windows XP, Windows Vista, Windows 10, Windows 8, Linux, BSD, SunOS, Solaris, Android, iOS, BlackBerry OS, or other compatible operating systems. In Macintosh systems, the operating system may be any available operating system, such as MAC OS X. In other embodiments, the computing system 1000 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 10, the computing system 1000 is coupled to a network 1016, such as a LAN, WAN, or the Internet, for example, via a wired, wireless, or combination of wired and wireless, communication link 1014. The network 1016 communicates with various computing devices and/or other electronic devices via wired or wireless communication links. In the embodiment of FIG. 10, the network 1016 is communicating with one or more computing systems 1017 and/or one or more data sources 1019.

Access to the atypical data detection system module 1006 of the computer system 1000 by computing systems 1017 and/or by data sources 1019 may be through a web-enabled user access point such as the computing systems' 1017 or data source's 1019 personal computer, cellular phone, smartphone, laptop, tablet computer, e-reader device, audio player, or other device capable of connecting to the network 1016. Such a device may have a browser module that is implemented as a module that uses text, graphics, audio, video, and other media to present data and to allow interaction with data via the network 1016.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 1012 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1000 may comprise a physical or logical connection established between a remote microprocessor and a mainframe host computer for the express purpose of uploading, downloading, or viewing interactive data and databases on-line in real time. The remote microprocessor may be operated by an entity operating the computer system 1000, including the client server systems or the main server system, an/or may be operated by one or more of the data sources 1019 and/or one or more of the computing systems 1017. In some embodiments, terminal emulation software may be used on the microprocessor for participating in the micro-mainframe link.

In some embodiments, computing systems 1017 who are internal to an entity operating the computer system 1000 may access the atypical data detection system module 1006 internally as an application or process run by the CPU 1002.

User Access Point

In an embodiment, a user access point or user interface comprises a personal computer, a laptop computer, a tablet computer, an e-reader device, a cellular phone, a smartphone, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, a smartphone, a smartwatch, or the like.

Other Systems

In addition to the systems that are illustrated in FIG. 10, the network 1016 may communicate with other data sources or other computing devices. The computing system 1000 may also comprise one or more internal and/or external data sources. In some embodiments, one or more of the data repositories and the data sources may be implemented using a relational database, such as DB2, Sybase, Oracle, Code-Base and Microsoft® SQL Server as well as other types of databases such as, for example, a flat file database, an entity-relationship database, and object-oriented database, and/or a record-based database.

Overview of Atypicality

One characteristic of the information age is the exponential growth of information, and the ready availability of this information through networks, including the internet (e.g., "Big Data"). The question is what to do with this enormous amount of information. One possibility is to characterize it through statistics, such as averages. Some techniques disclosed herein, however, are different, or the opposite, and consider that most of the value in the information may be in the parts that deviate from the average, that are unusual, atypical. Think of art: the valuable paintings or writings are those that deviate from the norms, that are atypical. The same could be true for venture development and scientific research. In Donald Rumsfeld's infamous words: "There are known knowns; there are things we know that we know. There are known unknowns; that is to say there are things that, we now know we don't know. But there are also unknown unknowns—there are things we do not know, we don't know." One of the benefits of the systems and techniques disclosed herein is to find these 'unknown unknowns.'

What is an atypical sequence? Consider throwing a fair coin. If we get a sequence a 100 consecutive heads, we would be surprised. If we were in a casino, security would scrutinize our gambling. Yet, a sequence of 100 consecutive heads does not contradict the laws of probability for a fair coin. In fact, for a fair coin the sequence of 100 consecutive heads has exactly the same probability as any other sequence. In terms of counting heads a simple test for atypicality could be to compare the ratio of heads with ½, and declare it atypical if the deviation is above a certain threshold. But the sequence HTHTHTHT . . . is also intuitively atypical, and would surely also raise eyebrows in a casino, although the ratio is ½. Thus, a deeper approach to the problem is needed.

We disclose herein various ways of approaching atypicality. To summarize, one important way to find atypical data in large datasets is to define a sequence as atypical if it can be described (coded) with fewer bits in itself rather than using the (optimum) code designed for typical sequences (referred to herein sometimes as "Definition 1"). This definition is central to our approach to the atypicality problem; however, rather than using it as a strict definition, we generally use it as a guiding principle. Definition 1 has two parts that work in concert, and we can write it simplified as $C_t(x) - C_a(x) > 0$.

While relatively straightforward to state, this definition is rather deep, and not quite straightforward to implement, which is why the systems and techniques disclosed herein have been developed. Considering the above coin toss examples, this principle works as follows. For 100 consecutive heads, we can describe it simply by saying '100 heads,' which is much shorter than listing each toss. Similarly, the sequence HTHTHTHT . . . can be described simply as '50 of HT.' Thus, these sequences, which are intuitively atypical, are found by our principle. It should be clear to one of skill in the art that a real world application of this principle (such as on ECG data) is much more complex than simply analyzing 100 coin tosses.

There are an incredible array of applications to the systems and techniques disclosed herein, a small fraction of which are mentioned presently, including but not limited to ECG. There are patterns in heart rate variability, signal amplitude, or a variety of other data variables that are known or may be known in the future to indicate possible heart disease. One can analyze a large collection of ECG recordings and look for individuals with atypical patterns. This can then be used to develop new diagnostic tools (such as, for example, the systems discussed above). Numerous other medical applications are also possible. In some embodiments, atypicality can be utilized to detect disease or risk of disease by analysis of electroencephalograms (EEGs) for seizure, brain tumors, consciousness, drug overdose, encephalitis, stroke, migraines, sleep disturbances, or other diseases. Atypicality can be utilized to analyze imaging data, including X-ray, ultrasound, CT, MRI, and PET scan data (including but not limited to mammograms, pap smears, and other data); as well as pathology images, such as biopsy images or real-time in situ images utilizing endoscopes, for example. Atypicality can be utilized to analyze genetic data, including genes, DNA and RNA, for example. Stock Market. Atypicality can be used to detect insider trading. It can also be used by investors to find unusual stocks to invest in, promising outstanding returns—or ruin. Computer Networks. Atypical network traffic can be indicative of a cyberattack; systems and methods can also be utilized to locate and decrypt encrypted data, e.g., cracking codes. Electric Power Grids. Atypicality can be used to detect unusual activity that may be indicative of imminent grid failure. Credit card fraud. Unusual spending patterns can be indicative of fraud. This is already used by credit card companies, but obviously in a simple, and annoying way (e.g., methods that do not use atypicality), as anyone who's credit card has been blocked on an overseas trip can testify to.

One can think of atypicality as a methodology to find anomalies in data, although we think of the applications as broader than traditional anomaly detection, as data discovery. Past anomaly detection methods have been based on examining specific features of data (e.g., to find known knowns or known unknowns). However, in order to find 'unknown unknowns' more innovative and universal methods are needed. Two options follow.

In a first example, a probability model of typical data is given, and an input is a test sequence x. First, a system calculates the code length CT(x) of x given the probability model of typical data, for example using and arithmetic coder. Second, the system calculates the code length CA(x) using any universal source coder. When calculating CA(x), desirably all terms needed for decoding should be included, for example to encode header and length. This is not necessarily a requirement however. Finally, the system compares CA(x) to CT(x), and if CA(x) is less than CT(x), the test sequence x is considered atypical. In other words, if the encoded length using any universal source coder is less than the encoded length using the arithmetic coder, the test sequence x is detected as atypical.

In a second example, training data y is a given and a test sequence x is the input. First, the system trains any universal source coder with the given training data y. Second, the system freezes the universal source coder. Next, the system calculates the code length CT(x|y) of x given the training data with the source coder frozen. Next, the system calculates the code length CA(x) using any universal source coder, including potentially the same universal source coder. However, this source coder is not frozen and/or has not been trained on the training data y. As before, when calculating CA(x), desirably all terms needed for decoding should be included, for example to encode header and length. This is not, however, required. The system finally compares the encoded lengths CA(x) to CT(x|y). If encoded length CA(x) is less than encoded length CT(x|y), the sequence X is detected as atypical. Example embodiments of using these two example techniques in a more complicated setting are given above, with reference to the process flow embodiments shown in FIGS. 4, 6, 8, and 9. These techniques can be vastly beneficial to enabling the finding of a large proportion of anomalies in a universal way. One purpose of detecting atypicality is to alert an observer to unusual data, which the observer can then examine using further information.

Binary IID Case

As an example, we present a binary IID case. To summarize we have:

$$L_t = l\left(\hat{p}\log\frac{1}{p} + (1-\hat{p})\log\frac{1}{1-p}\right) - \log\epsilon \quad (1)$$

$$L_a = lH(\hat{p}) + \frac{1}{2}\log l + \log^* l + \log c - \log\epsilon - \log\delta \approx$$

$$lH(\hat{p}) + \frac{3}{2}\log l - \log\epsilon + \tau$$

$$\tau = -\log\delta + \log c$$

Where $\epsilon$ is the probability of a new sequence starting, and $\delta$ the probability of this being atypical. The criterion for a sequence to be atypical is $L_a < L_t$, or $$D(\hat{p}\|p) > \frac{\tau + \frac{3}{2}\log l}{l} \quad (2)$$

To implement fast detection, first we rewrite (2) as $$D_{n,l} = l\left(\hat{p}_{n,l}\log\frac{1}{p} + (1-\hat{p}_{n,l})\log\frac{1}{1-p}\right) - \left(lH(\hat{p}_{n,l}) + \frac{3}{2}\log l\right) \quad (3)$$

$$\hat{p}_{n,l} = \frac{1}{l}\sum_{i=n-l+1}^{n} X_i$$

$$D_{n,l} > \tau$$

The first phase is detection. For every n we then calculate $D_{n,l}$ and test (3). The problem is that this has very high complexity as we would like to use large values of l. We are therefore looking for a low-complexity, approximate algorithm for detection.

We first consider the following heuristic approach. We use the set of lengths $l \in L = \{2^i, i=0 \ldots i_{max}\}$ and calculate $D_{kl,i}, k \in Z, l \in L$. This will clearly not catch all atypical sequences. Heuristically one can argue that the worst case is when an atypical sequence of length $l \square L$ is divided into two segments. In that case, at least one segment of length $l/2$ is included in the atypical sequence. The threshold for length $l$ 2 sequences is different than for length l sequences. This can be compensated for by using double length in (3), that is, calculating $$\tilde{D}_{n,l} = 2l\left(\hat{p}_{n,l}\log\frac{1}{p} + (1-\hat{p}_{n,l})\log\frac{1}{1-p}\right) - \left(2lH(\hat{p}_{n,l}) + \frac{3}{2}\log 2l\right) \quad (4)$$

$$\hat{p}_{n,l} = \frac{1}{l}\sum_{i=n-l+1}^{n} X_i$$

$$\tilde{D}_{n,l} > \tau$$

There will of course still be a certain miss probability as well as a false alarm probability.

Next, to implement segmentation, an algorithm should take a string and the P(x=1) of that string as input (T as an input is optional). If P(x=1)>½, replace all the ones with zero and replace all the zeros with one. For each n, find the smallest l satisfying (4). Do the next two step as long as it's needed (two iteration is sufficient):

We set $n_1=n-l+1$ and $n_2=n$, for $n_1$ we try to find smallest $n_2$ bigger than n which minimize $$\sum_{i=n_1}^{n_2} X_i \log\frac{p}{\hat{p}} + \sum_{i=n_1}^{n_2}(1-X_i)\log\frac{1-p}{1-\hat{p}} + \frac{3}{2}\log(n_2-n_1+1) + \tau$$

For $n_2$ we try to find the biggest $n_1$ smaller than $n_2$ which minimize $$\sum_{i=n_1}^{n_2} X_i \log\frac{p}{\hat{p}} + \sum_{i=n_1}^{n_2}(1-X_i)\log\frac{1-p}{1-\hat{p}} + \frac{3}{2}\log(n_2-n_1+1) + \tau$$

Recursive coding: Definition 1 can be applied to encoded sequences instead of the original data.

Non-IID Case

As another example, we present a non-IID case. In terms of coding, Definition 1 can be stated in the following form $$C(x|P)-C(x)>0 \quad (5)$$

Here C(x|P) is the code length of x encoded with the optimum coder according to the typical law, and C(x) is x encoded 'in itself.' As argued in the above section relating to the binary IID case, we desirably need to put a 'header' in atypical sequences to inform the encoder that an atypical encoder is used. We can therefore write $$C(x)=\tau+\tilde{C}(x)$$

where $\tau$ is the number of bits for the 'header,' and $\tilde{C}(x)$ is the number of bits used for encoding the data itself.

Typical Encoding: We write the typical encoding as C(x|y), where y is training data and the encoder is a universal source coder, for example CTW algorithm. To understand what this means, we have to realize that when x is encoded according to C(x|P), the coding probabilities are fixed. Thus, when we estimate the coding probabilities, those estimates should be for the typical data, but not be affected by the atypical data—we desirably need to 'freeze' the source coder. The equation (5) then becomes $$C(x|y)-C(x)>0$$

Atypical subsequences: For finding atypical subsequences of long sequences, the same basic setup as in the previous sections can be used. The start of a sequence desirably needs to be encoded as well as the length, and additionally the code length is minimized over the maximum depth D of the context tree. The code length is then given by $$L_A(\chi) = \min_D(-\log P_\omega^\lambda(D) + \log^* D) + \log^* l + \tau$$

Where $P_w^\lambda(D)$ is the probability at the root of the CTW tree. We desirably need to test every subsequence of every length. For maximum performance, a new CTW algorithm desirably needs to be started at every sample time. So, if the total length of the sequence is L, in principle L separate CTW trees need to be maintained. These are completely independent, so they could be run on parallel processors.

Simplified Implementation: We use the simplified implementation from the section above. One way of looking at this approach is as follows. Divide the data into segments of fixed length $l_i=2^i$. To compensate for the fact that an atypical subsequence can be divided into two, we repeat each segment of $l_i$ twice. In the IID case, this is equivalent to using 2l where ever l appears. For a model with k parameters, the same approach could be used, for example changing the cost of encoding the parameters from k/2 log l to k/2 log 2l. The issue now is that CTW and other source coding algorithms do not calculate the redundancy terms explicitly. Simply repeating the segment and applying source coding will not work either, since an exact repeated segment can be encoded very efficiently.

We have therefore developed the following approach. First, another way to look at the approach above is as follows. If an atypical segment is cut in two, the part that is not seen has the same structure as the part that is seen; but it is not identical. The IID coder does not discover that the segment is identical, it only discovers that the probabilities are the same, i.e., the same structure. But a universal source coder will discover that it is identical. To simulate the behavior of the IID coder, we take the following approach for the CTW. Suppose that we have encoded $\{x_1, \ldots, x_n\}$. Recall that $P_w^\lambda(n)$ (with index n added here) denotes the (coding) probability of the sequence $\{x_1, \ldots, x_n\}$. With a new sample $x_{n+1}$, $P_w^\lambda(n)$ is the probability of the sequence $\{x_1, \ldots, x_{n+1}\}$. Therefore $$\frac{P_w^\lambda(n+1)}{P_w^\lambda(n)}$$

can be interpreted as the conditional probability $P(x_{n+1}|x_n, \ldots, x_1)$. Now, instead of simply repeating the bit $x_{n+1}$ we generate a new bit $\hat{x}_{n+1}$ according to the distribution $P(x_{n+1}|x_n, \ldots, x_1)$. This is then encoded according to the CTW coding probability, but it is not added to the context. That is we encode $x_1\hat{x}_1 x_2\hat{x}_2, \ldots$ but for encoding $x_n\hat{x}_n$ the context $x_1, \ldots, x_{n-1}$.

Example Algorithm: Here we present an example embodiment of an algorithm for detecting atypical sequences (in this case for cardiac patterns, but could be applied elsewhere as well). One of skill in the art will recognize that this process may be modified in various ways without departing from the spirit of the present disclosure.

First the data is scanned, and the empirical distribution of the data is calculated. This distribution is used to encode the data with a Huffman code (though other codes could be used). Instead of a usual prefix-free code, we desirably use a suffix-free code, as context trees rely on suffixes of sequences. Further processing is done on this data, which is in principle equivalent to processing the original data according to the section above.

For every bit of the data we calculate $$\Delta L(n) = \min_l L_A(\chi(l)) - L_T(\chi(l))$$

where $X(l)=\{X(n-l), \ldots X(n)\}$, and where $L_A(X(l))$ is calculated with $\tau=0$. In a practical sense, it doesn't make much sense to consider bits in the middle of a beat. Therefore, $\Delta L(n)$ is desirably only calculated at the end of each encoded beat difference (though could in other embodiments be calculated elsewhere as well).

We now test $\Delta L(n) > \tau$ for increasing values of $\tau$. We choose $\tau$ so that we get a reasonable number of subsequences declared atypical.

For the given $\tau$, we now segment the whole sequence into typical and atypical segments by minimizing total code length as described above.

Notice that in some embodiments the above processes might be repeated, as the complexity is low. Perhaps at first we choose a high value of $\tau$ to only look at the most atypical sequences. If we find something there, we might decrease $\tau$ to get more sequences and so on.

Cybersecurity

As mentioned above, cyber security is another use of the systems, methods, and devices disclosed herein. For example, an atypical data detection system as disclosed herein may be utilized to analyze network traffic for atypical patterns (and desirably previously unknown atypical patterns) that may potentially be indicative of a cyber-attack or other suspicious or harmful activity. This can be more efficient and effective than alternative methods, such as comparing network activity against known patterns of suspicious activity. In one example embodiment, a cyber-attack detection system is included as a part of a computer network. The cyber-attack detection system can comprise, for example, a router device, a server, a network appliance, a desktop computer, a virtual computer, and/or the like. The cyber-attack detection system can be configured to monitor data, such as, for example, Ethernet packets, Wi-Fi data packets, and/or the like that pass to, from, and/or within the computer network. In some embodiments, the system can be configured to analyze the data contained in these packets using techniques similar to those described above, for example, with respect to the process flow examples given in FIGS. 8 and 9. The system can be configured to analyze this data to detect atypical patterns, and optionally analyze those atypical patterns to determine if they are potentially a sign of a pending cyber-attack or other unauthorized network access, intrusion, or suspicious activity.

It should be noted that, although it can be useful to process the actual content of network data packets (e.g., the payload as opposed to the header information) in detecting atypical data, processing and/or analyzing the contents or payload of the network packets is not a requirement. For example, it may be more efficient in some cases to operate an atypical data or atypical pattern detection system that desirably primarily analyzes header information and/or other characteristics of network traffic, such as metadata related to the packets, data content type, data content size, receiver, sender, time of sending, interval between sending different packets, and/or the like. Further, in some embodiments, the content of a network data packet may be encrypted, and, depending on the specific setup, may not be decryptable by the system that is monitoring the traffic for atypicalities. However, using the techniques disclosed herein, a system can still detect atypical network activity that may be indicative of, for example, a cyber-attack or other potential harmful or malicious activity without even needing to know what is in the encrypted content of the packets. In some embodiments, however, the system is configured to analyze the contents of a data packet, either unencrypted data or after decrypting the data, either alone or in combination with other information related to the data packet, such as metadata, header information, and/or the like.

With reference to the example process flow described above and given in FIG. 9, the data source 906 may be, for example, network data packets. At block 904, where that raw data is collected, the cyber-attack detection system may, for example, intercept that data, such as by operating as a man in the middle or through other means. For example, the cyber-attack detection system may comprise a firewall through which all or most network traffic must pass. In some embodiments, the cyber-attack detection system comprises a firewall through which only data being sent to and/or from the network must pass, but that internal network traffic may not necessarily need to pass through. In other embodiments, the system comprises a firewall through which all traffic, even internal traffic must pass. In some embodiments, the system does not necessarily need traffic to pass through it, but the system is configured to monitor traffic as that traffic passes through other portions of the network.

At block 910, the raw data in some embodiments would not need to be digitized, because network traffic is typically already a digital form of data or information. However, the techniques disclosed herein could still be used with an analog network, were such a network to be used. In that case, the analog data would be digitized at block 910.

Block 912 comprises optionally converting digital data to a lower bit dataset. For example, the system may be configured to convert the logged or monitored data packets to a lower bit dataset, such as through compression or other means. For example, one interesting feature of the logged data packets may be a size of a header, a size of the overall packet, a time between receiving packets from a particular sender or that are directed to a particular receiver, and/or a variety of other potential characteristics or metadata related to such packets. In some embodiments, the raw data may be compressed or converted by utilizing one or more of these pieces of information, similarly to how the cardiac activity data is converted in the process flow of FIG. 4 by calculating inter-beat times.

At block 916, an empirical distribution is optionally calculated on the raw or converted data. For example, this may be beneficial if the first encoder used at block 918 is, for example, a probabilistic encoder. Similarly to as described above, at blocks 918 through 924, a first calculation of an encoded bit length using a first encoder, such as a typical encoder, is calculated. A second calculation of an encoded bit length using a second encoder, such as a universal encoder, is also calculated. The two encoded lengths are compared, such as by subtracting one from the other, and atypical network traffic has been detected if the encoded length using the second encoder, such as a universal encoder, is shorter than the encoded length using the first encoder, such as a typical encoder or a trained and frozen universal encoder.

The remainder of the process shown in FIG. 9 can operate as described above, for example, by processing detected atypical segments to determine if they are a potential threat, storing identified or processed atypical segments in a known patterns database to enable the system to learn and/or reduce false positives, and/or the like.

In some embodiments, a computer-implemented method for detecting atypical network activity comprises: selecting, by a computer system, a data set for analysis to determine atypical data within the data set, the data set comprising data related to logged network activity; generating, by the computer system, a first encoded length of a segment of the data set using a first encoder; generating, by the computer system, a second encoded length of the segment of the data set using a second encoder; comparing, by the computer system, the first and second encoded lengths; determining that the second encoded length is smaller than the first encoded length, wherein the second encoded length being smaller than the first encoded length is indicative of an atypical pattern; processing the atypical pattern to validate that the atypical pattern is indicative of suspicious network activity, wherein processing the atypical pattern comprises one or more of: probing one or more network resources (e.g., computer devices connected to the network), analyzing the atypical pattern in conjunction with a known patterns database, and/or the like; wherein the computer system comprises one or more computer processors and an electronic memory. In some embodiments, the method further comprises automatically updating the known patterns database with the detected atypical pattern to increase operating efficiency and/or to reduce future false positives. In some embodiments, the method further comprises automatically reporting the detected atypical pattern and/or the validated atypical pattern via, for example, a network message, an email, a text message, a phone call, a audible alert, a visual alert and/or message, and/or various other types of electronic communication and/or notification. In some embodiments, such a method is one embodiment of systems, methods, and devices for cyber security using atypicality for improved discovery and detection of anomalies.

It should be noted that, although various embodiments disclosed herein discuss using universal source coding techniques to detect atypicality, the concepts disclosed herein may be used with other techniques, too. For example, signal processing principles may be used rather than universal source coding.

Some embodiments of the systems, methods, and devices that have been disclosed herein are enabled by (and/or the problems they solve are caused by) the fact that computer technology has been developed that enables gathering, storing, and/or monitoring of vast amounts of data or information. Gathering such vast and detailed amounts of information is not something that was possible before computers, when things were done manually or by hand. The introduction of computers, and particularly ever more powerful computers, ever-increasing storage space, and the increasing ease with which computers can communicate over computer networks has created both these opportunities to monitor and analyze vast quantities of data and associated problems, such as in the cybersecurity realm. Accordingly, some embodiments of the techniques disclosed herein are necessarily rooted in computer technology to overcome problems specifically arising in the realm of computer networks and other computer technology. Further, some embodiments of the techniques disclosed herein are not able to be performed manually, either in a human's head or, for example, with paper and pencil.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A cardiac diagnostic system for detecting potential indicators of cardiac disease, the cardiac diagnostic system comprising:
   a cardiac monitoring device comprising at least one electrode configured to detect an analog electrical cardiac signal of a user;
   a cardiac signal filter configured to convert the analog electrical cardiac signal to digital electrocardiogram data; and
   an atypical cardiac sequence detector configured to analyze the digital electrocardiogram data to detect atypical cardiac patterns that are potentially indicative of cardiac disease,
   wherein detecting the atypical cardiac patterns comprises:
      determining a first encoded length of a segment of the digital electrocardiogram data using a first encoder based on typical data;
      determining a second encoded length of the segment of the digital electrocardiogram data using a second encoder without knowledge of typical data, so that the encoded data is decodable; and
      comparing the first and second encoded lengths,
      wherein the second encoded length being smaller than the first encoded length is indicative of an atypical cardiac pattern.

2. The cardiac diagnostic system of claim 1, further comprising:
   an atypical cardiac sequence processor configured to analyze detected atypical cardiac patterns in conjunction with historical data to determine whether the detected cardiac patterns are indicative of cardiac disease.

3. The cardiac diagnostic system of claim 2, wherein the atypical cardiac sequence processor is further configured to generate an alert when a detected atypical cardiac pattern is determined to be indicative of cardiac disease.

4. The cardiac diagnostic system of claim 1, wherein the first encoder comprises a typical encoder and the second encoder comprises a universal encoder.

5. The cardiac diagnostic system of claim 1, wherein the first encoder comprises a universal encoder that has been trained and frozen.

6. The cardiac diagnostic system of claim 5, wherein the second encoder comprises the same universal encoder, but not having been frozen.

7. The cardiac diagnostic system of claim 1, wherein the atypical sequence detector is further configured to store a detected pattern in a known patterns database.

8. The cardiac diagnostic system of claim 1, wherein detecting the atypical cardiac patterns further comprises:
   determining a difference in the first and second encoded lengths;
   comparing the determined difference to a threshold value; and
   flagging the segment as atypical when the determined difference is greater than the threshold value.

9. The cardiac diagnostic system of claim 1, further comprising one or more computer processors configured to operate the cardiac signal filter and atypical cardiac sequence detector.

10. A cardiac diagnostic system for detecting potential indicators of cardiac disease, the cardiac diagnostic system comprising:
    an atypical cardiac sequence detector configured to analyze digital electrocardiogram data to detect atypical cardiac patterns that are potentially indicative of cardiac disease, the digital electrocardiogram data generated by a cardiac signal filter configured to convert analog electrical cardiac signals to digital data, the analog electrical cardiac signals detected by at least one electrode of a cardiac monitoring device,
    wherein detecting the atypical cardiac patterns comprises:
       determining a first encoded length of a segment of the digital electrocardiogram data using a first encoder based on typical data;
       determining a second encoded length of the segment of the digital electrocardiogram data using a second encoder without knowledge of typical data, so that the encoded data is decodable; and
       comparing the first and second encoded lengths,
       wherein the second encoded length being smaller than the first encoded length is indicative of an atypical cardiac pattern.

11. The cardiac diagnostic system of claim 10, further comprising:
    an atypical cardiac sequence processor configured to analyze detected atypical cardiac patterns in conjunction with historical data to determine whether the detected cardiac patterns are indicative of cardiac disease.

12. The cardiac diagnostic system of claim 11, wherein the atypical cardiac sequence processor is further configured to generate an alert when a detected atypical cardiac pattern is determined to be indicative of cardiac disease.

13. The cardiac diagnostic system of claim 10, wherein the first encoder comprises a typical encoder and the second encoder comprises a universal encoder.

14. The cardiac diagnostic system of claim 10, wherein the first encoder comprises a universal encoder that has been trained and frozen.

15. The cardiac diagnostic system of claim 14, wherein the second encoder comprises the same universal encoder, but not having been frozen.

16. The cardiac diagnostic system of claim 10, wherein the atypical sequence detector is further configured to store a detected pattern in a known patterns database.

17. The cardiac diagnostic system of claim 10, wherein detecting the atypical cardiac patterns further comprises:
   determining a difference in the first and second encoded lengths;
   comparing the determined difference to a threshold value; and
   flagging the segment as atypical when the determined difference is greater than the threshold value.

18. The cardiac diagnostic system of claim 10, further comprising one or more computer processors configured to operate the atypical cardiac sequence detector.

19. A cardiac diagnostic method for detecting potential indicators of cardiac disease, the cardiac diagnostic method comprising:
   receiving, by a computer system, digital electrocardiogram data representative of electrical cardiac activity, the digital electrocardiogram data generated by converting analog electrical cardiac signals to digital data, the analog electrical cardiac signals detected by at least one electrode of a cardiac monitoring device;
   selecting, by the computer system, a segment of the digital electrocardiogram data to analyze for potential atypical cardiac patterns;
   determining, by the computer system, a first encoded length of the segment of the digital electrocardiogram data using a first encoder based on typical data;
   determining, by the computer system, a second encoded length of the segment of the digital electrocardiogram data using a second encoder without knowledge of typical data, so that the encoded data is decodable; and
   comparing, by the computer system, the first and second encoded lengths,
   wherein the second encoded length being smaller than the first encoded length is indicative of an atypical cardiac pattern, and
   wherein the computer system comprises one or more computer processors and an electronic memory.

20. The cardiac diagnostic method of claim 19, wherein the first encoder comprises a typical encoder and the second encoder comprises a universal encoder.

* * * * *